(12) United States Patent
Vogt et al.

(10) Patent No.: US 10,517,662 B2
(45) Date of Patent: Dec. 31, 2019

(54) DEVICE FOR MIXING AND STORING POLYMETHYLMETHACRYLATE BONE CEMENT

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 604 days.

(21) Appl. No.: 15/171,460

(22) Filed: Jun. 2, 2016

(65) Prior Publication Data
US 2016/0354129 A1    Dec. 8, 2016

(30) Foreign Application Priority Data
Jun. 3, 2015   (DE) .................. 10 2015 108 783

(51) Int. Cl.
*A61B 17/88* (2006.01)
*B01F 13/00* (2006.01)
(Continued)

(52) U.S. Cl.
CPC .......... *A61B 17/8833* (2013.01); *A61L 27/02* (2013.01); *A61L 27/16* (2013.01);
(Continued)

(58) Field of Classification Search
CPC ......... A61B 17/8833; A61B 2017/8838; B01F 11/0054; B01F 13/0023; B01F 13/003;
(Continued)

(56) References Cited

U.S. PATENT DOCUMENTS

| 4,671,263 A | 6/1987 | Draenert |
| 4,758,096 A | 7/1988 | Gunnarsson |

(Continued)

FOREIGN PATENT DOCUMENTS

| DE | 36 40 279 A1 | 6/1987 |
| DE | 200 05 333 U1 | 8/2001 |

(Continued)

OTHER PUBLICATIONS

Charnley, "Anchorage of the Femoral Head Prosthesis to the Shaft of the Femur"; The Journal of Bone and Joint Surgery; 42 (1960) pp. 28-30.

(Continued)

*Primary Examiner* — Marc C Howell
(74) *Attorney, Agent, or Firm* — Norris McLaughlin, P.A.

(57) ABSTRACT

A device and methods mix polymethylmethacrylate bone cement and/or store the starting components of the bone cement. The device comprising: a cartridge with an internal space for mixing the bone cement that is closed on one side by means of a mobile dispensing plunger; a monomer container for a monomer liquid and/or a connector for attachment of a monomer container for a monomer liquid such that the monomer container can be opened appropriately in the device such that the monomer liquid flows from the monomer container into the device; a connecting conduit through which the monomer liquid can be guided into the internal space of the cartridge. A first hollow cylinder is connected to the connecting conduit and a second hollow cylinder is connected, via a vacuum conduit, to the internal space of the cartridge, whereby a pumping plunger is shiftable axially in the first hollow cylinder and is arranged in the first hollow cylinder and a vacuum plunger that is shiftable axially in the second hollow cylinder is arranged in (Continued)

the second hollow cylinder, whereby the pumping plunger and the vacuum plunger may be moved simultaneously.

34 Claims, 9 Drawing Sheets

(51) Int. Cl.
*B01F 15/02* (2006.01)
*A61L 27/02* (2006.01)
*A61L 27/16* (2006.01)

(52) U.S. Cl.
CPC ...... *B01F 13/0023* (2013.01); *B01F 15/0278* (2013.01); *A61B 2017/8838* (2013.01); *A61L 2430/02* (2013.01); *B01F 2215/0029* (2013.01)

(58) Field of Classification Search
CPC .................. B01F 13/06; B01F 15/0206; B01F 2215/0029; B01F 15/0237; B01F 15/0278; B01F 15/0279; A61L 27/02; A61L 27/16; A61L 2430/02
USPC .......................................... 366/139
See application file for complete search history.

(56) References Cited

U.S. PATENT DOCUMENTS

| | | |
|---|---|---|
| 4,973,168 A | 11/1990 | Chan |
| 5,100,241 A | 3/1992 | Chan |
| 5,344,232 A | 9/1994 | Nelson et al. |
| 5,551,778 A | 9/1996 | Hauke et al. |
| 5,586,821 A | 12/1996 | Bonitati et al. |
| 5,588,745 A | 12/1996 | Tanaka et al. |
| 5,624,184 A | 4/1997 | Chan |
| 5,997,544 A | 12/1999 | Nies et al. |
| 6,033,105 A | 3/2000 | Barker et al. |
| 6,120,174 A | 9/2000 | Hoag et al. |
| 6,709,149 B1 | 3/2004 | Tepic |
| 6,796,701 B2 | 9/2004 | Wahlig et al. |
| 7,073,936 B1 | 7/2006 | Jonsson |
| 8,128,276 B2 | 3/2012 | Axelsson et al. |
| 8,662,736 B2 | 3/2014 | Vogt et al. |
| 8,757,866 B2 | 6/2014 | Vogt et al. |
| 9,334,147 B2 | 5/2016 | Vogt et al. |
| 2003/0021180 A1* | 1/2003 | Wahlig ............... A61B 17/8827 366/139 |
| 2008/0037365 A1 | 2/2008 | Axelsson et al. |
| 2010/0329074 A1* | 12/2010 | Vogt .................. A61B 17/8825 366/190 |
| 2012/0006874 A1 | 1/2012 | Vogt et al. |
| 2015/0367301 A1 | 12/2015 | Vogt |

FOREIGN PATENT DOCUMENTS

| | | |
|---|---|---|
| DE | 698 12 726 T2 | 2/2004 |
| DE | 10 2009 031 178 B3 | 9/2010 |
| DE | 10 2010 026 496 B4 | 5/2014 |
| EP | 0 692 229 A1 | 1/1996 |
| EP | 1 005 901 A2 | 7/2000 |
| EP | 1 016 452 A2 | 7/2000 |
| EP | 1 020 167 A2 | 7/2000 |
| EP | 1 259 200 B1 | 8/2005 |
| EP | 1 886 647 A1 | 2/2008 |
| EP | 2 957 337 A1 | 12/2015 |
| WO | 94/26403 A1 | 11/1994 |
| WO | 99/67015 A1 | 12/1999 |
| WO | 00/35506 A1 | 6/2000 |

OTHER PUBLICATIONS

European Search Report from corresponding EP application 16169158.9 dated Oct. 17, 2016.
Australian Patent Examination Report No. 1 from correspoding application 2016202959 dated Oct. 24, 2016.

\* cited by examiner

DEVICE FOR MIXING AND STORING POLYMETHYLMETHACRYLATE BONE CEMENT

This application claims foreign priority benefit under 35 U.S.C. § 119 of German Application No. DE 10 2015 108 783.9, filed Jun. 3, 2015.

The invention relates to a mixing system for the mixing of polymethylmethacrylate bone cement (PMMA bone cement) from two starting components, in particular for the mixing of a medical bone cement, and for storage of the starting components.

The invention further relates to a method for the mixing of polymethylmethacrylate bone cement.

Accordingly, the object of the invention is a device for storage and mixing of polymethylmethacrylate bone cement and method for the mixing of polymethylmethacrylate bone cement.

Polymethylmethacrylate (PMMA) bone cements are based on the pioneering work of Sir Charnley (Charnley, J.: Anchorage of the femoral head prosthesis of the shaft of the femur. J. Bone Joint Surg. 42 (1960) 28-30). PMMA bone cements consist of a liquid monomer component and a powder component. The monomer component generally contains the monomer, methylmethacrylate, and an activator (N,N-dimethyl-p-toluidine) dissolved therein. The powder component, which is also referred to as bone cement powder, comprises one or more polymers, a radiopaquer, and the initiator dibenzoylperoxide. The polymers of the powder component are produced on the basis of methylmethacrylate and comonomers, such as styrene, methylacrylate or similar monomers by means of polymerisation, preferably by suspension polymerisation. During the mixing of powder component and monomer component, swelling of the polymers of the powder component in the methylmethacrylate generates a dough that can be shaped plastically and is the actual bone cement. During the mixing of powder component and monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

Methylmethacrylate is the monomer used most commonly in polymethylmethacrylate bone cements. Redox initiator systems usually consist of peroxides, accelerators and, if applicable, suitable reducing agents. Radicals are formed only if all ingredients of the redox initiator systems act in concert. For this reason, the ingredients of the redox initiator system in the separate starting components are arranged appropriately such that these cannot trigger a radical polymerisation. The starting components are stable during storage provided their composition is adequate. Only when the two starting components are mixed to produce a cement dough, the ingredients of the redox initiator system, previously stored separately in the two pastes, liquids or powders react with each other forming radicals which trigger the radical polymerisation of the at least one monomer. The radical polymerisation then leads to the formation of polymers while consuming the monomer, whereby the cement dough is cured.

PMMA bone cements can be mixed by mixing the cement powder and the monomer liquid in suitable mixing beakers with the aid of spatulas. Said procedure is disadvantageous in that air inclusions might arise and/or be present in the cement dough thus formed, which may have a detrimental effect on the mechanical properties of the cured bone cement and might cause destabilisation of the bone cement later on.

A large number of vacuum cementing systems has been proposed for preventing air inclusions in bone cement dough of which the following shall be specified here for exemplary purposes: U.S. Pat. Nos. 6,033,105 A, 5,624,184 A, 4,671, 263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, U.S. Pat. No. 5,344,232 A. The vacuum cementing systems thus specified, need to have an external vacuum pump connected to them in order to generate the negative pressure. These are generally operated by compressed air utilising the Venturi principle. The compressed air required for operation of the vacuum pumps is supplied either by stationary compressed air facilities or by electrically-operated compressors. In addition, it is also feasible to use electrically-operated vacuum pumps to generate vacuum.

Cementing systems, in which both the cement powder and the monomer liquid are already packed in separate compartments of the mixing systems and are mixed with each other in the cementing system only right before application of the cement, are a development of cementing technology. Said closed full-prepacked mixing systems were proposed through EP 0 692 229 A1, DE 10 2009 031 178 B3, U.S. Pat. Nos. 5,997,544 A, 6,709,149 B1, DE 698 12 726 T2, and U.S. Pat. No. 5,588,745 A. Said mixing systems also require an external vacuum source. A device for the mixing of bone cement, in which the vacuum can be generated by means of a manual pump and in which a monomer liquid is injected by means of a syringe that can be connected to it, is known from EP 1 259 200 B1. However, the system described therein is not a full-prepacked mixing system and, in addition, is associated with a disadvantage in that the vacuum pump and the syringe containing the monomer liquid need to be manually connected to the device in laborious manner. The various requisite handling steps make the device rather time-consuming to handle.

Patent DE 10 2009 031 178 B3 discloses a generic mixing system having a two-part dispensing plunger for the closing of a cement cartridge. A combination of a gas-permeable sterilisation plunger and a gas-impermeable sealing plunger is used in this context. This principle of a closed vacuum mixing system is implemented in the closed cementing system, PALACOS® PRO, made and distributed by Heraeus Medical GmbH.

WO 00/35506 A1 proposes a device, in which the polymethylmethacrylate bone cement powder is stored in a cartridge, whereby the cement powder takes up the entire volume of the cartridge and the volume of the intervening spaces between the particles of the cement powder is equal to the volume of the monomer liquid required for the production of bone cement dough using the cement powder stored in the cartridge. The design of said device is appropriate such that the action of a vacuum causes the monomer liquid to be supplied into the cartridge from above, whereby a vacuum is applied to a vacuum connector on the underside of the cartridge for this purpose. As a result, the monomer liquid is aspirated through the cement powder, whereby the air present in the intervening spaces of the cement particles is replaced by the monomer liquid. This involves no mechanical mixing of the cement dough thus formed by means of a stirrer.

It is a disadvantage of the system that cement powders, which swell quickly due to the monomer liquid, cannot be mixed with said device, because the rapidly swelling cement powder particles form a gel-like barrier of approximately 1 to 2 cm after ingress of the monomer liquid into the cement powder and impede the migration of the monomer liquid through the entire cement powder. Moreover, employing the action of a vacuum, it cannot be excluded that the monomer liquid is suctioned off through the vacuum connector after it fully penetrates the cement powder. In this case, there a sufficient amount of monomer liquid for curing by means of radical polymerisation is no longer available and/or the mixing ratio and thus the consistency of the bone cement is changed inadvertently. Moreover, it is a problem that the air trapped between the cement powder particles is to be displaced by the monomer liquid proceeding from top to bottom, because the air, having a lower specific weight than the monomer liquid, tends to migrate upwards in the cement powder rather than downwards in the direction of the vacuum connector under the force of gravity.

If vacuum mixing systems are used for cementing, external vacuum pumps need to be provided in most cases. Said vacuum pumps are expensive and need to be cleaned after use. Moreover, vacuum hoses for connecting the vacuum pumps to the vacuum mixing systems are required. Said vacuum hoses need to be enclosed with the vacuum mixing systems. Accordingly, prior to the mixing using a vacuum mixing system, the vacuum pump first needs to be set-up in the surgical theatre (OR) and must be connected to an energy source, such as compressed air or electrical power. Then, the vacuum pump is connected to the vacuum mixing system by means of a vacuum hose. Said installation steps take up costly OR time and are potentially error-prone. The vacuum pump and connecting conduits to the vacuum mixing system and to external energy sources and supply conduits take up space and are potential tripping hazards and stumbling blocks that can disturb the often hectic procedure during a surgery.

An interesting concept has been proposed through EP 1 886 647 A1. Here, the cement powder is stored in an evacuated cartridge and the monomer liquid is situated in a separate container. The cartridge, which is kept at a negative pressure, being opened causes the monomer liquid to be aspirated into the cartridge without any ingress of air. A bone cement dough free of air inclusions is thus produced. Said concept requires the cartridge to remain closed in vacuum-tight manner during the storage before use such that no non-sterile air can enter into the cartridge. For this purpose, the cartridge must be hermetically sealed in a stable manner. Accordingly, one associated disadvantage is that the design is quite elaborate and that the content of the cartridge cannot be mixed by an externally-operated mixing system after aspiration of the monomer liquid since a feed-through for a mixing rod or for a mixing tube would not readily be permanently vacuum-tight.

Accordingly, it is the object of the invention to overcome the disadvantages of the prior art. In particular, the disadvantages of the known vacuum mixing systems with external vacuum source and/or elaborate design and elaborate operation are to be overcome. It is one of the objects of the invention to develop a simple closed device, in which polymethylmethacrylate bone cement powder (cement powder) and monomer liquid can be stored in separate compartments and can be mixed with each other subsequently. It shall be possible for the medical user to combine and mix the polymethylmethacrylate bone cement powder (PMMA bone cement powder) and the monomer liquid inside the device, without the medical user being exposed to both cement components. Exposure of the medical user to the polymethylmethacrylate bone cement powder and to the monomer liquid shall be excluded as much as possible. The device to be developed is a full-prepacked mixing system. The nature of the device shall be appropriate such that the monomer liquid can be transferred into the polymethylmethacrylate bone cement powder without the use of external vacuum pumps driven by compressed air or compressors. It is also important that the device ensures the production of bone cement doughs functionally and reliably without the use of external energy sources, such as compressed air, vacuum or electrical current, even under the simplest external conditions. It shall be possible to use the device autonomously without any additional technical equipment. Moreover, the design shall be as simple and inexpensive as possible. It shall be possible to operate the device easily even under difficult conditions.

Moreover, it is an object of the invention to provide a device, in which the volume of monomer liquid transferred into the cement powder can be controlled specifically such that the ratio of the volume of monomer liquid to the quantity of cement powder can be varied in order to control the consistency and thus the processing properties of the bone cement. Moreover, air bubbles shall be prevented from being present in the ready-mixed bone cement.

Moreover, a method is to be provided that enables a monomer transfer and a mixing in full-prepacked mixing systems. In this context, it shall be possible to manufacture the mixing system (the device) to be developed mainly from inexpensive plastics.

Moreover, a device that is inexpensive to manufacture and works reliably for the mixing of a medical cement and, if applicable, for storage of the starting components of the cement, and a method for the mixing of the bone cement is to be devised, in which a simple manual operation can be used to mix the starting components, if possible without having to use an external or additional energy source and without air inclusions arising in the mixing material.

The main component of the polymethylmethacrylate bone cement, as mixing material, shall be a powder and the second component shall be present in the form of a liquid. Preferably, it shall be possible to store the two starting components of the bone cement separate from each other in the full-prepacked mixing system and to combine them safely through the use of the device.

The objects of the invention are met by a device for the mixing of polymethylmethacrylate bone cement and for storage of the starting components of the bone cement, in particular of a monomer liquid and a cement powder, as starting components of the bone cement, the device comprising A) a cartridge with an internal space for mixing the bone cement that is closed on one side by means of a mobile dispensing plunger;

B) a monomer container for a monomer liquid and/or a connector for attachment of a monomer container for a monomer liquid such that the monomer container can be opened appropriately in the device such that the monomer liquid flows from the monomer container into the device;

C) a connecting conduit through which the monomer liquid can be guided into the internal space of the cartridge, whereby D) a first hollow cylinder is connected to the connecting conduit and a second hollow cylinder is connected, via a vacuum conduit, to the internal space of the cartridge, whereby a pumping plunger that can be shifted axially in the first hollow cylinder is arranged in the first hollow cylinder and a vacuum plunger that can be shifted axially in the second hollow cylinder is arranged in the second hollow cylinder, whereby, according to the invention, the pumping plunger and the vacuum plunger can be moved simultaneously.

In particular, the pumping plunger and the vacuum plunger can be movable synchronous to each other.

It is particularly preferable to design the first and the second hollow cylinder as a shared hollow cylinder, inside of which a combined pumping/vacuum plunger moves, whereby a first side, in particular the underside, of the pumping-vacuum plunger forms the pumping plunger and a second side, in particular the upper side, of the pumping-vacuum plunger forms the vacuum plunger. In this case, the upper part of the shared hollow cylinder shall be considered to be the second hollow cylinder and the lower part of the shared hollow cylinder shall be considered to be the first hollow cylinder in the scope of the present invention.

In order for the monomer liquid to flow from the opened monomer container into the first hollow cylinder, the opened monomer container is connected to the first hollow cylinder, preferably is connected to the first hollow cylinder by means of a junction.

For the monomer liquid to flow without any additional action of a force, the device must be set up properly such that gravity effects the desired direction of flow. Accordingly, the terms, top, and, bottom, and, above, and, below, and, highest, and, lowest, as used in the scope of the present invention shall be understood to always relate to the device being set-up properly.

Preferably, the internal space of the cartridge has a cylindrical geometry. The cylindrical geometry is the simplest geometry that allows the internal space of the cartridge and the first and the second hollow cylinder to be implemented. A cylindrical internal space shall be understood geometrically to mean the shape of a general cylinder with any footprint, i.e. not just a cylinder with a circular footprint. Accordingly, the internal wall of the internal space can be a cylinder of any footprint and the jacket of the first and second hollow cylinder can be a cylinder of any footprint, i.e. including a non-circular or round footprint. However, a cylindrical geometry with a rotationally symmetrical footprint is preferred according to the invention.

In order to attain a good pumping effect and prevent the monomer liquid from leaking from the pumping plunger and/or the first hollow cylinder, the pumping plunger closes, such as to be fluid-tight, against the internal walls of the first hollow cylinder. A circumferential seal that closes the pumping plunger with respect to the internal walls of the first hollow cylinder can be provided for this purpose. Likewise, a circumferential seal can be provided in order to seal the vacuum plunger with respect to the internal walls of the second hollow cylinder such that no or at least very little air is drawn from the other side of the vacuum plunger, when a negative pressure is generated with the vacuum plunger.

It is preferred, according to the invention, to have the monomer container be connected to the connector for the monomer container or to have the monomer container be inserted in the connector for the monomer container.

Preferably, the polymethylmethacrylate bone cement is mixed and/or can be produced from at least two components. Particularly preferably, one component is liquid (the monomer liquid) and the other component is powdered (the cement powder).

According to the invention, the starting components for the mixing material, in particular for the PMMA bone cement, are already present in the cartridge and the monomer container.

It is preferred, according to the invention, that the device is also well-suited for storage of the starting components, in particular when the containers, in particular the monomer container, are inserted into the device or the containers, in particular the monomer container, are a fixed part of the device.

The device according to the invention can also be provided such that the pumping plunger and the vacuum plunger are connected to each other appropriately or are moved by means of a shared operating element such that, when the pumping plunger is being slid into the first hollow cylinder, the vacuum plunger in the second hollow cylinder moves away from the connection to the vacuum conduit, whereby the volume between the vacuum plunger and the connection to the vacuum conduit in the second hollow cylinder preferably enlarges such that the negative pressure arising in the second hollow cylinder causes a gas to flow from the internal space of the cartridge through the vacuum conduit into the second hollow cylinder.

The enlargement of the volume between the vacuum plunger and the connection to the vacuum conduit in the second hollow cylinder is associated with the generation of a negative pressure that draws gas from the internal space of the cartridge through the vacuum conduit into the second hollow cylinder and/or such that gas is being pushed from the internal space of the cartridge through the vacuum conduit into the second hollow cylinder.

As a result, a single motion causes the monomer liquid to be pushed from the hollow cylinder into the internal space of the cartridge and causes the air to be drawn from the internal space of the cartridge.

Moreover, the invention can provide the first hollow cylinder to be connected to the monomer container and/or the connector for attachment of a monomer container in appropriate manner such that the monomer liquid flows from the opened monomer container or an opened attached monomer container into the first hollow cylinder and such that the connecting conduit connects the first hollow cylinder to the internal space of the cartridge in appropriate manner such that the pumping plunger can be used to push monomer liquid from the first hollow cylinder through the connecting conduit into the internal space of the cartridge by actuating the pumping plunger.

This ensures that the device can be designed in simple and easy manner and without additional components or an electronic regulation or control. This allows the device to be used in places without energy supply.

Moreover, the invention can provide the first hollow cylinder to be arranged between the monomer container or the connector for the monomer container and the internal wall of the cartridge. In this context, the invention can preferably provide the first hollow cylinder to be arranged in the connecting conduit between the monomer container or the connector for the monomer container and the internal wall of the cartridge.

This allows to dispense with an additional conduit and there is no need for re-plugging the connecting conduit. This simplifies the application of the device even more.

The first hollow cylinder being arranged between the monomer container for the monomer liquid or the connector for the monomer liquid and the cartridge does not mean that the hollow cylinder is geometrically arranged in between these, but is arranged between arranged between the monomer container for the monomer liquid or the connector for the monomer liquid and the cartridge with respect to the liquid connections, i.e. with respect to the flow direction of the monomer liquid flowing and/or being pumped from the opened monomer container in the direction of the cartridge.

A refinement of the present invention proposes the pumping plunger and the first hollow cylinder to comprise a smaller cross-sectional area than the vacuum plunger and the second hollow cylinder, preferably the vacuum plunger and the second hollow cylinder to comprise a cross-sectional area at least twice as large as the pumping plunger and the first hollow cylinder.

As a result, a larger amount of gas can be evacuated from the internal space of the cartridge by the vacuum plunger. Concurrently, the force expended to actuate the pumping plunger is not too large such the device, in particular the pumping plunger and vacuum plunger connected to each other, can easily be operated by hand.

The invention can just as well provide the pumping plunger and the vacuum plunger to be connected to each other, preferably to be affixed to each other, particularly preferably to be designed as a single part.

This attains a particularly stable and simple design.

In this context, the invention can just as well provide the side of the vacuum plunger facing the vacuum conduit to be arranged on the rear side of the pumping plunger and, correspondingly, the side of the pumping plunger facing the connecting conduit to be arranged on the rear side of the vacuum plunger.

Accordingly, according to the invention, the pumping plunger and the vacuum plunger can be implemented in the form of a shared pumping-vacuum plunger, which simplifies the design of the device. Moreover, this implements a two-side plunger principle that is particularly easy to apply, in which both sides of the combined pumping-vacuum plunger and/or both front faces of the combined pumping-vacuum plunger are used to perform the work based on a joint motion, namely both the pumping of the monomer liquid into the internal space of the cartridge and the generation of a negative pressure for evacuation of the internal space of the cartridge.

The invention further proposes to have the vacuum conduit connected to the internal space of the cartridge by means of the dispensing plunger, whereby the dispensing plunger preferably has a filter or a screen arranged in it by means of which the vacuum conduit is connected to the internal space of the cartridge.

Preferably, the dispensing plunger has a two-part design that includes a sterilisation plunger and a feed plunger, whereby the sterilisation plunger and the feed plunger can be connected to each other.

As a result, the connector for the vacuum conduit can earlier be used for evacuation and for sterilization with a gas. Moreover, the connector is thus arranged opposite from a dispensing opening of the cartridge through which the monomer liquid is also pushed into the internal space of the cartridge, i.e. into which the connecting conduit merges into the internal space of the cartridge. As a result, the negative pressure can aspirate the monomer liquid into the cartridge and thus support the filling of the cartridge with the monomer liquid even more.

A refinement of the present invention can provide the monomer container to be arranged or arrangeable in a flexible ampoule container, whereby it is preferable to provide at least one ventilation opening in the ampoule container.

As a result, it is easy to open an ampoule as monomer container by bending the ampoule container and thus breaking the ampoule such as to be open. The ventilation opening helps the monomer liquid to flow out easily. Moreover, the at least one ventilation opening can be used for sterilisation of the device with ethylene oxide.

According to a preferred refinement, the present invention can provide a mixing facility that can be operated from outside to be arranged in the cartridge, whereby the mixing facility preferably can be operated by means of a mixing rod that is guided through a feed-through in the dispensing plunger into the interior of the cartridge and is supported such as to be mobile.

It is particularly preferable for the mixing rod to be supported such that it can be rotated in the feed-through and can be shifted in longitudinal direction. The content of the internal space of the cartridge can be mixed conveniently with the mixing rod of the mixing facility. Referring to the use of low viscosity bone cements, the use of a mixing rod and a mixing facility is dispensable, because the monomer liquid displaces the air of the pore spaces between the cement powder particles and wets the cement powder particles before the cement powder swells.

The invention can just as well provide the dispensing plunger to be impermeable for powders, whereby it is preferred to arrange a pore filter in the dispensing plunger that is permeable for gas and impermeable for powder.

It is preferable to design the pore filter as pore disk. The impermeability for powder prevents the cement powder from leaking from the interior of the cartridge. If the dispensing plunger is gas-permeable, the internal space can be evacuated through the dispensing plunger and can be sterilised with a gas, such as, for example, ethylene oxide. The vacuum conduit preferably merges via the dispensing plunger, in particular via the pore disk, into the internal space of the cartridge.

Preferably, the invention can just as well provide the internal space of the cartridge to contain the cement powder.

The invention can just as well provide the monomer container to contain the monomer liquid. As a result, the device is a ready-made full-prepacked mixing system that does not need to be filled with the cement powder prior to use. Prior to use, the cement powder is stored in the cartridge separate from the monomer liquid.

The invention also proposes a filter that is impermeable for the cement powder and permeable for the monomer liquid to be arranged between the connecting conduit and the internal space of the cartridge.

As a result, the cement powder can be prevented from ingress into the connecting conduit and from polymerising in this place when the monomer liquid is supplied and thus can be prevented from inadvertently clogging and/or blocking, like a glue, the connecting conduit.

Preferred embodiments can provide the device to comprise a base, in which at least a part of the connecting conduit is arranged, whereby the cartridge is connected to the base in detachable manner, in particular is connected to the base in detachable manner by means of a screw thread, whereby the filter, if any, that is impermeable for the cement powder and permeable for the monomer liquid is arranged in the base of the device, particularly preferably is arranged in the connection to the cartridge of the base.

As a result, the device is easy to set up and operate.

In this context, the invention can provide the first hollow cylinder, the second hollow cylinder, and the monomer container or the first hollow cylinder, the second hollow cylinder, and the connector for attaching the monomer container to be connected to the base, preferably to be connected to the base in non-detachable manner.

As a result, a particularly simple and inexpensive design of the device is attained.

The present invention also proposes the monomer container for the monomer liquid or the connector for attaching the monomer container to merge into the first hollow cylinder on a jacket surface of the first hollow cylinder, preferably to merge into the first hollow cylinder right below the pumping plunger.

As a result, it can be ensured that the monomer liquid can completely flow into the hollow cylinder and can fill the hollow cylinder. Moreover, air can exit from the hollow cylinder particularly easily at this site.

Moreover, the invention can provide the device to comprise opening means for opening the monomer container by means of which the monomer container can be opened inside the device, whereby it is preferred to have a screen or a filter arranged in the connection to the first hollow cylinder by means of which fragments or shreds of the opened monomer container can be retained.

Preferably, the invention can provide the monomer container to be a breakable glass ampoule in this context.

The opening means being a part of the device allows the device to also be used for long-term storage of the monomer. A suitable opening means is known, for example, from the DE 10 2010 026 496 B4 patent.

Moreover, the invention can provide the monomer container to be arranged above the connection to the first hollow cylinder.

By this means, the monomer liquid can flow from the monomer container into the first hollow cylinder due to the action of gravity after the monomer container is opened. Alternatively, the monomer container could just as well be squeezed out and the monomer could thus flow into the first hollow cylinder.

Preferred devices can also be characterised in that the connecting conduit is connected to the first hollow cylinder on the lower side, preferably is connected to the first hollow cylinder on the lowest point of the first hollow cylinder, whereby it is particularly preferred to have the pumping plunger be arranged on the opposite side of the first hollow cylinder.

As a result, the monomer liquid can be made to flow and/or can be pushed completely out of the first hollow cylinder by means of the pumping plunger.

Moreover, the invention proposes the first hollow cylinder to comprise, on the side opposite from the pumping plunger, a conical, semi-spherical or otherwise downwards-tapering bottom, whereby the surface of the pumping plunger facing the bottom of the first hollow cylinder preferably is a negative mould of the bottom.

As a result, the monomer liquid can be made to flow and/or can be pushed completely out of the first hollow cylinder by means of the pumping plunger. This means that all of the monomer liquid flows to the lowest point of the first hollow cylinder and that there are no "dead" regions, in which monomer liquid remains behind when the pumping plunger is actuated. Since the shape of the pumping plunger is adapted to the inner shape of the first hollow cylinder, all of the monomer liquid is pressed out of the first hollow cylinder through the pumping plunger when the pumping plunger is moved in the direction of the opening to the connecting conduit without any residual monomer liquid remaining in the first hollow cylinder. Moreover the shape of the front face of the pumping plunger being conical or spherical and/or fitting ensures that, when the pumping plunger moves downward and/or in the direction of the base, the air above the monomer liquid in the first hollow cylinder can escape through the opening in the jacket surface of the first hollow cylinder and no air bubbles remain above the monomer liquid during transfer of the monomer liquid into the internal space of the cartridge and/or into the cement powder.

Preferred devices according to the invention can also be characterised in that the pumping plunger can be moved axially in the first hollow cylinder by hand, preferably can be pressed axially into the first hollow cylinder by hand and/or the vacuum plunger can be moved axially in the second hollow cylinder by hand.

By this means, it is feasible to press the monomer liquid out of the first hollow cylinder by hand and to transfer it into the internal space of the cartridge and/or to generate the vacuum in the second hollow cylinder by hand in order to evacuate air from the cartridge.

To simplify the operation and to increase the variability of devices according to the invention, the invention can just as well provide the first hollow cylinder to be transparent and to comprise markings indicating the filling level of a liquid in the first hollow cylinder.

As a result, an amount of the monomer liquid determined by the markings can be filled into the first hollow cylinder and/or can be pressed from the first hollow cylinder into the internal space of the cartridge. This provides an opportunity to use the device to produce a bone cement dough of a consistency that is predetermined by the amount of the monomer liquid. Alternatively, the first hollow cylinder can just as well be non-transparent and markings can be provided on an operating element of the pumping plunger and/or vacuum plunger projecting from the housing of the device in order to be able to enable defined propulsion of the pumping plunger and thus to be able to press a defined volume of the monomer liquid from the first hollow cylinder. Accordingly, said designs allow the entire volume of the monomer liquid to be pressed from the first hollow cylinder into the cement powder in the internal space of the cartridge as well as to transfer just certain partial volumes of the monomer liquid from the first hollow cylinder into the cement powder. As a result, the ratio of monomer liquid and amount of powder can be adjusted, which allows the time at which the cement dough thus formed becomes non-tacky and the viscosity of the bone cement to be controlled specifically.

The invention can just as well provide the first hollow cylinder and/or the second hollow cylinder to comprise an internal thread and the pumping plunger and/or the vacuum plunger to comprise a matching external thread such that the pumping plunger and/or the vacuum plunger can be screwed into the first hollow cylinder and/or the second hollow cylinder in order to press the monomer liquid out of the first hollow cylinder into the internal space of the cartridge and/or to draw air out of the internal space of the cartridge into the second hollow cylinder.

This also allows a defined amount of the monomer liquid to be pressed out of the hollow cylinder into the internal space of the cartridge. This provides an opportunity to use the device to produce a bone cement dough of a consistency that is determined by the amount of the monomer liquid. Moreover, the negative pressure in the second hollow cylinder can be generated by a large force. Concurrently, having the thread present reduces the risk of the vacuum plunger inadvertently moving in the direction of the connector to the vacuum conduit due to the negative pressure. If the vacuum plunger has a larger cross-section than the pumping plunger, which is preferred according to the invention, it may suffice to have only the vacuum plunger comprise an external thread that can be screwed into an internal thread of the second hollow cylinder. This applies especially when the pumping plunger and the vacuum plunger are designed as a shared pumping-vacuum plunger.

Moreover, the invention can provide the device to comprise at least one tensioned compression spring and at least one locking mechanism, whereby the compression spring, the vacuum plunger and/or the pumping plunger is or are locked by means of the at least one locking mechanism in detachable manner, whereby the at least one compression spring, with the locking mechanism detached, exerts a pressure on the pumping plunger and/or the vacuum plunger such that the pumping plunger is pressed into the first hollow cylinder and/or the vacuum plunger is pushed away from the connector to the vacuum conduit in the second hollow cylinder.

Referring to the embodiment, in which the first and/or second hollow cylinder comprise an internal thread and the pumping plunger and/or the vacuum plunger comprise an external thread, at least one tensioned volute spring can be provided in analogous manner, which screws the pumping plunger into the first hollow cylinder and/or the vacuum plunger into the second hollow cylinder after detachment of at least one locking mechanism.

These measures are advantageous in that they simplify the operation of the device. Moreover, possible operating errors can thus be prevented.

Moreover, the invention can provide the dispensing plunger to be connected to the cartridge by means of a detachable snap-in device, whereby the snap-in device can be detached by hand, in particular through the action of an axial force, such that the dispensing plunger can be moved axially in the internal space of the cartridge.

As a result, the dispensing plunger can be prevented from moving inadvertently such as may be caused by a vacuum or a negative pressure in the internal space of the cartridge.

The invention also proposes the connecting conduit between the first hollow cylinder and the internal space of the cartridge to comprise a loop that faces upwards, whereby the topmost point of the loop is situated above a junction of the monomer container or of the connector for the monomer container into the first hollow cylinder.

This can prevent the monomer liquid from already reaching the internal space of the cartridge via the connecting conduit while it is being filled into the first hollow cylinder. The effect of the connecting conduit having said U-shaped loop is that the monomer liquid in the first hollow cylinder remains in the connecting conduit up to the level of the apex before the pumping plunger is moved in the direction of the connecting conduit, which prevents premature ingress of the monomer liquid to the cement powder. In particular in the case of high viscosity cements, premature contact even of small volumes of monomer liquid with the cement powder can block, like a glue, the connecting conduit or a conduit means provided as a nozzle, as is described in U.S. Pat. No. 8,662,736 B2. The connecting conduit can be transparent or translucent to allow the user to visually check the monomer transfer. For this purpose, in particular, an inspection window, through which the loop with the highest apex can be seen, can be provided in the device.

Moreover, the invention can provide the volume in the first hollow cylinder to be smaller than or equal to the volume of the monomer liquid in the monomer container.

As a result, air is prevented from being pressed along into the cement powder when the pumping plunger is being actuated.

Moreover, the invention can provide the internal space of the cartridge to be connected, on the lower side, to the connecting conduit in liquid-permeable manner.

In the front face of the internal space, the connecting conduit can merge into a nozzle in accordance with U.S. Pat. No. 8,662,736 B4. Said nozzle prevents the entry of cement powder into the connecting means.

The objects underlying the present invention are also met by a method for the mixing of bone cement, in particular with the device according to the invention, comprising the chronological steps of A) a monomer container being opened, B) a monomer liquid flowing from the monomer container into a first hollow cylinder, whereby the first hollow cylinder is bounded on one side by a pumping plunger, C) the pumping plunger being pushed into the first hollow cylinder and the monomer liquid thus being pressed out of the first hollow cylinder and through a connecting conduit into the internal space of a cartridge, whereby a cement powder is situated in the internal space of the cartridge, D) the motion of the pumping plunger moving a vacuum plunger, which is connected to the pumping plunger or driven parallel to same, in a second hollow cylinder away from a connector of a vacuum conduit, whereby the gas pressure between the connector of the vacuum conduit and the vacuum plunger in the second hollow cylinder is reduced due to the motion of the vacuum plunger and gas is evacuated, through the vacuum conduit, from the internal space of the cartridge that is connected to the vacuum conduit, and E) the monomer liquid and the cement powder being mixed in the internal space of the cartridge.

Preferably, the monomer liquid flows into the hollow cylinder due to the action of gravity.

In this context, the invention can provide the monomer liquid and the cement powder to be mixed in the internal space of the cartridge only once the pumping plunger has been pushed in fully or up to a marking in the first hollow cylinder, whereby the marking is a measure of the [amount of] monomer liquid supplied into the internal space of the cartridge.

As a result, it can be made sure by means of the desired admixture of monomer liquid that the bone cement dough thus generated has the desired consistency.

Methods according to the invention can also be provided appropriately such that the air is aspirated from the internal space of the cartridge through the vacuum conduit on the side opposite from the junction of the connecting conduit, whereby it is preferred to have the connecting conduit merge into the internal space of the cartridge on the underside of the internal space and to have the vacuum conduit merge into the internal space of the cartridge on the upper side of the internal space.

As a result, it can be made sure that the monomer liquid can be supplied into the internal space of the cartridge and the air can be evacuated from the internal space of the cartridge simultaneously. Moreover, this can prevent the monomer liquid from inadvertently ingressing into the vacuum conduit.

Moreover, the invention proposes the monomer liquid and the cement powder to be mixed in the internal space by means of a mixing facility by operating the mixing facility by moving a mixing rod that extends into the internal space of the cartridge and can be rotated and can be shifted in longitudinal direction, whereby it is preferred to pull the mixing rod out of the internal space of the cartridge up to the limit stop after the mixing and it is particularly preferred to break off the mixing rod at a predetermined breakage site after pulling it out to the limit stop.

As a result, the method can be implemented through manual operation.

Moreover, the invention can provide the monomer container to be opened through operating a triggering and opening means, whereby it is preferred to have the monomer container be broken open by the opening means.

As a result, the monomer container can be opened inside the device such that the entire device can be closed with respect to the outside.

Moreover, the invention can provide the pumping plunger to be pushed into the first hollow cylinder by means of a tensioned elastic spring element and/or the vacuum plunger to be moved in the second hollow cylinder by means of a tensioned elastic spring element, whereby it is preferred to first detach at least one locking mechanism that engages or engage the pumping plunger, the vacuum plunger and/or the spring element for this purpose.

This attains further automation of the method according to the invention and also prevents potential operating errors.

The invention can just as well provide the cartridge containing the ready-mixed cement dough to be detached from the connecting conduit, vacuum conduit, first hollow cylinder, second hollow cylinder and monomer container, and the ready-mixed cement dough to be dispensed from the internal space of the cartridge through propulsion of a dispensing plunger, which is supported in the cartridge such as to be axially mobile and forms a boundary of the internal space of the cartridge on one side.

The invention is based on finding, surprisingly, that a monomer liquid can be pressed into the internal space of a cartridge from below by means of a pumping plunger and that a negative pressure can be generated in the internal space of the cartridge by concurrently moving a vacuum plunger in a hollow cylinder such that no interfering air inclusions are formed in the bone cement. Concurrently, set device allows to largely dispense with external energy sources or internal energy accumulators since the pumping plunger and the vacuum plunger can be operated by hand. In particular, no vacuum sources and connectors and components that are vacuum-tight in the long term need to be used, which simplifies the use in less-developed places as well as local use or use in field hospitals significantly. Moreover full-prepacked mixing systems according to the invention are less susceptible to possible disturbances and are therefore highly likely to be ready for use, since no vacuum leaks can occur.

For example, a device according to the invention and/or a method according to the invention can be provided appropriately such that, after a monomer container is opened, the monomer liquid flows into a hollow cylinder due to the action of gravity, [and] is then pressed from same into the internal space of the cartridge containing cement powder through manual actuation of the pumping plunger. This means that the transfer of monomer liquid proceeds through the action of a pressure rather than a vacuum, which is in contrast to the previous commercial mixing systems. A manually actuated monomer transfer effected by the action of a pressure can be implemented inexpensively using simple plastic parts that can be produced by injection moulding of plastics. Concurrently, a negative pressure is generated in the internal space of the cartridge by moving the vacuum plunger simultaneously in order to prevent or reduce the inclusion of air in the cement dough. The particular advantage of the device according to the invention is that the device can be operated without requiring external aids, such as compressed air-driven vacuum pumps, and without requiring external energy sources, such as compressed air or electrical power. As a result, the device according to the invention can be used autonomously and even under the most difficult surgery conditions. The device according to the invention provides a closed full-prepacked mixing system for price-sensitive markets.

In the scope of the present invention, it has been found that the supply of the monomer liquid into the cement powder from the underside of the internal space of the cartridge caused by pressure is associated with the monomer liquid migrating in the form of a uniform front from bottom to top. As a result, the air that is present in the intervening spaces between the cement powder particles is displaced and pushed out in upward direction. Concurrently, the air is actively drawn out through the motion of the vacuum plunger. Air inclusions are prevented or at least reduced by this means. In the scope of the present invention, it has been found that a bone cement dough produced with a device according to the invention and a method according to the invention is largely free of air inclusions and is of a quality that corresponds to the quality of a cement dough mixed under a vacuum.

An exemplary device according to the invention for storage and mixing of polymethylmethacrylate bone cement comprises a) a cartridge, whereby a first front side of the internal space of the cartridge is closed by at least one dispensing plunger that is impermeable for powder, and whereby the second front side of the internal space of the cartridge is impermeable for powder, by means of which the internal space of the cartridge, in which cement powder is arranged, bounded by the dispensing plunger and the second front face is formed;

b) whereby the internal space of the cartridge is connected to a cylindrical first hollow space in a first hollow cylinder by means of an opening that is impermeable for powder, permeable for liquid and has a liquid-permeable connecting conduit (conduit means)

c) whereby a liquid-permeable opening is arranged on the jacket surface of the first hollow cylinder and connects the first hollow space to an opening means for a monomer liquid container that is connected to a monomer liquid container that is arranged above the opening on the jacket surface of the first hollow cylinder;

d) a pumping plunger that is arranged in the cylindrical first hollow space and/or a combined pumping-vacuum plunger that can be shifted axially in the first hollow cylinder;

e) whereby the dispensing plunger is composed of a sealing plunger and a sterilisation plunger, whereby the sealing plunger is arranged above the sterilisation plunger, and the sealing plunger closes said internal space after being pushed into the internal space of the cartridge, and possesses a gas-permeable feed-through that connects the space below the sealing plunger to the space above the sealing plunger, whereby the feed-through is designed as a vacuum connector on the upper side;

f) whereby the first hollow cylinder is closed in gas-tight manner on its front face opposite from the foot part;

g) whereby a second hollow space is formed by the upper side of the pumping plunger and an extension of the hollow cylinder, which is closed in gas-tight manner on the front side, and/or a second hollow cylinder such that the upper side of the pumping plunger forms a vacuum plunger and thus a combined pumping-vacuum plunger is formed;

h) whereby a gas-permeable feed-through is provided in the front face of the second hollow cylinder, which is closed in gas-tight manner, and the gas-permeable feed-through is connected to the gas-permeable feed-through of the dispensing plunger and/or sealing plunger by means of a gas-permeable connecting means.

In this context, the pumping plunger and thus the vacuum plunger can be moved axially in the first and/or second hollow cylinder by means of a driving element that is guided in gas-tight manner.

The rationale of the idea is that, once a monomer container is opened with an opening device, for example a device in accordance with DE 10 2010 026 496 B4, the monomer liquid flows into the first hollow cylinder due to the action of gravity, [and] is then pressed from same into the cartridge containing cement powder through manual actuation of the pumping plunger. The first hollow cylinder and/or the second hollow cylinder is closed in gas-tight manner on its front face facing away from the foot part. When the vacuum plunger is moved in the direction of the foot part, whereupon the motion of the pumping plunger, in the case of a combined pumping-vacuum plunger, presses the monomer liquid into the internal space of the cartridge, a negative pressure is concurrently generated in the hollow space above the vacuum plunger in the second hollow cylinder. This means that a negative pressure is generated concurrently and is guided via a feed-through and via a gas-permeable connecting means (the vacuum conduit) into the internal space of the cartridge. If, during the motion of the pumping-vacuum plunger, the volume in the hollow space between the vacuum plunger and the connector to the vacuum conduit is larger than the volume of the monomer liquid in the first hollow cylinder to be pressed out, a negative pressure is generated in the first cartridge. This effect can be attained through providing the combined pumping-vacuum plunger to be made of two cylindrical plungers, namely the pumping plunger and the vacuum plunger, whereby the lower cylinder (pumping plunger) has a smaller external diameter than the upper cylinder (vacuum plunger). This means that the combined pumping-vacuum plunger is double-acting. Upon axial motion of the pumping-vacuum plunger, one side of the combined pumping-vacuum plunger has a pumping function for generating a positive pressure and the other side of the pumping-vacuum plunger concurrently generates a negative pressure.

According to another advantage of devices and methods according to the invention, a monomer transfer due to the expelling motion of the pumping plunger is always ensured to proceed regardless of whether or not the user closed the internal space of the cartridge in gas-tight manner with respect to the pumping plunger and/or vacuum plunger. As a result, the handling safety is increased as compared to previously known full-prepacked mixing systems, in which the transfer of the monomer liquid is effected only through the applied vacuum, which is more or less stable depending on the energy source that is used.

An exemplary method according to the invention is a method with the exemplary device described above that is characterised by the following steps proceeding in the order given, a) the monomer liquid container is opened by actuating the opening means;

b) the monomer liquid flows through the opening in the jacket surface of the first hollow cylinder into the hollow space of the first hollow cylinder due to the action of gravity;

c) following complete transfer of the monomer liquid into the hollow space of the first hollow cylinder, the pumping plunger and/or the combined pumping-vacuum plunger is pushed by hand in the direction of the foot part of the device;

d) whereby the monomer liquid is pushed through the connecting conduit (the conduit means) into the internal space of the cartridge into the cement powder;

e) following complete transfer of the monomer liquid from the first hollow space into the internal space of the cartridge, the mixture consisting of cement powder and monomer liquid is mixed by hand by actuating a mixing rod;

f) the mixing rod is then pulled upwards;

g) the mixing rod is then broken off at a predetermined breakage site; and h) the cartridge is then separated from the foot part.

Another exemplary method with the exemplary device described above that is characterised by the following steps proceeding in the order given, a) the monomer liquid container is opened by actuating the opening means;

b) the monomer liquid flows through the opening in the jacket surface of the first hollow cylinder into the hollow space of the first hollow cylinder due to the action of gravity;

c) following complete transfer of the monomer liquid into the first hollow space, a locking mechanism of the pumping plunger and/or of the combined pumping-vacuum plunger is detached whereby a compression spring pushes the pumping plunger and the vacuum and/or the combined pumping-vacuum plunger in the direction of the foot part of the device;

d) whereby the monomer liquid is pushed through the connecting conduit (the conduit means) into the internal space of the cartridge into the cement powder and the motion of the vacuum plunger and/or of the combined pumping-vacuum plunger draws air out of the internal space of the cartridge;

e) following complete transfer of the monomer liquid from the first hollow space into the internal space of the cartridge, the mixture consisting of cement powder and monomer liquid is mixed by hand by actuating a mixing rod;

f) the mixing rod is then pulled upwards;

g) the mixing rod is then broken off at a predetermined breakage site; and h) the cartridge is then separated from the foot part.

BRIEF DESCRIPTION OF THE DRAWINGS

Further exemplary embodiments of the invention shall be illustrated in the following on the basis of nine schematic figures, though without limiting the scope of the invention. In the figures.

DETAILED DESCRIPTION OF EMBODIMENTS

Sectioned surfaces are indicated by hatching in the cross-sectional views of FIGS. 3, 4, 6, 8, and 9.

Figure 1:
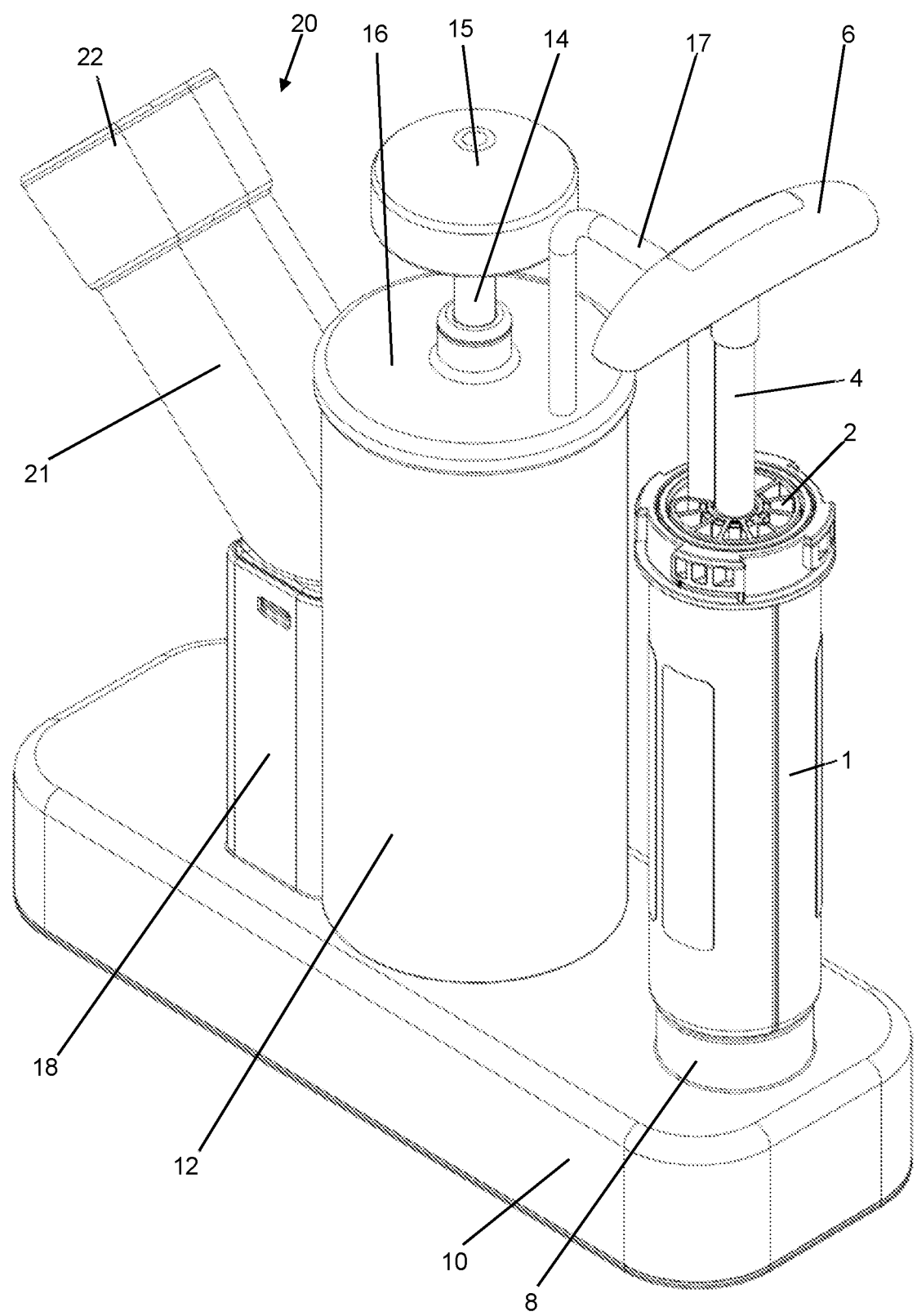
FIG. 1: shows a schematic perspective view of a device according to the invention as full-prepacked mixing system.
Figure 2:
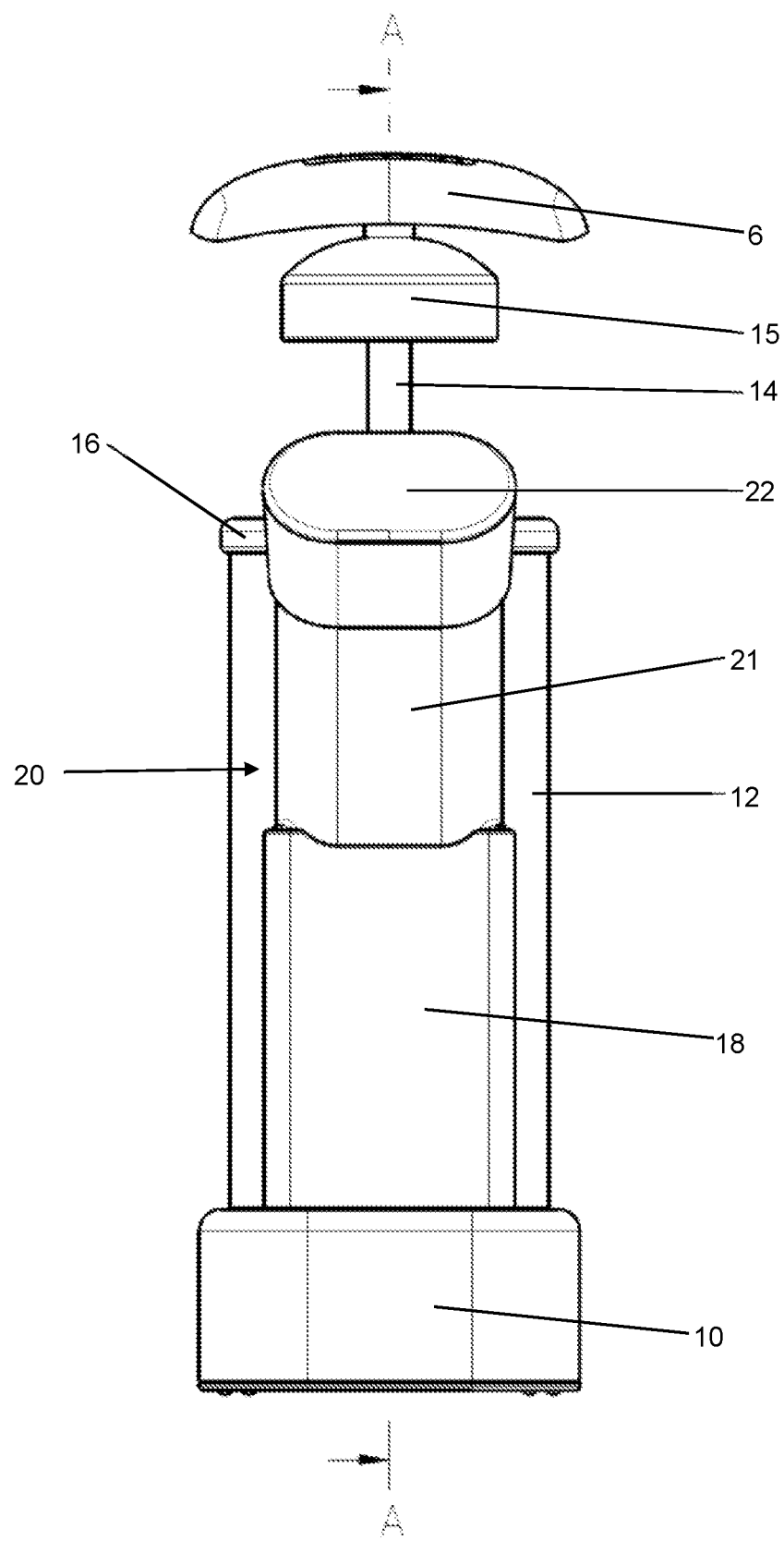
FIG. 2: shows the device according to FIG. 1 in a frontal view with a section plane AA.
Figure 3:
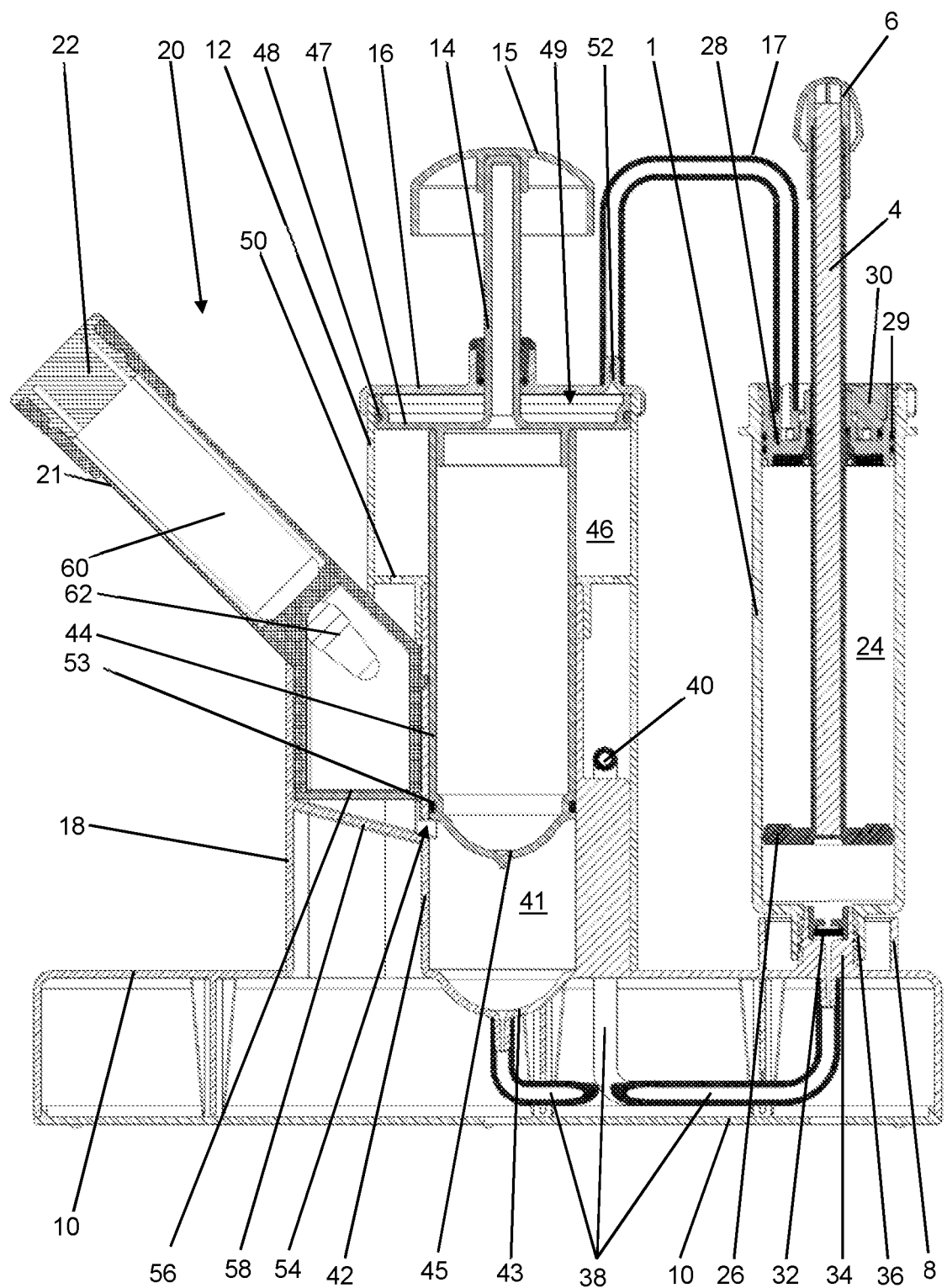
FIG. 3: shows the device according to FIGS. 1 and 2 in a schematic cross-sectional view that corresponds to section plane A in accordance with FIG. 2.
Figure 4:
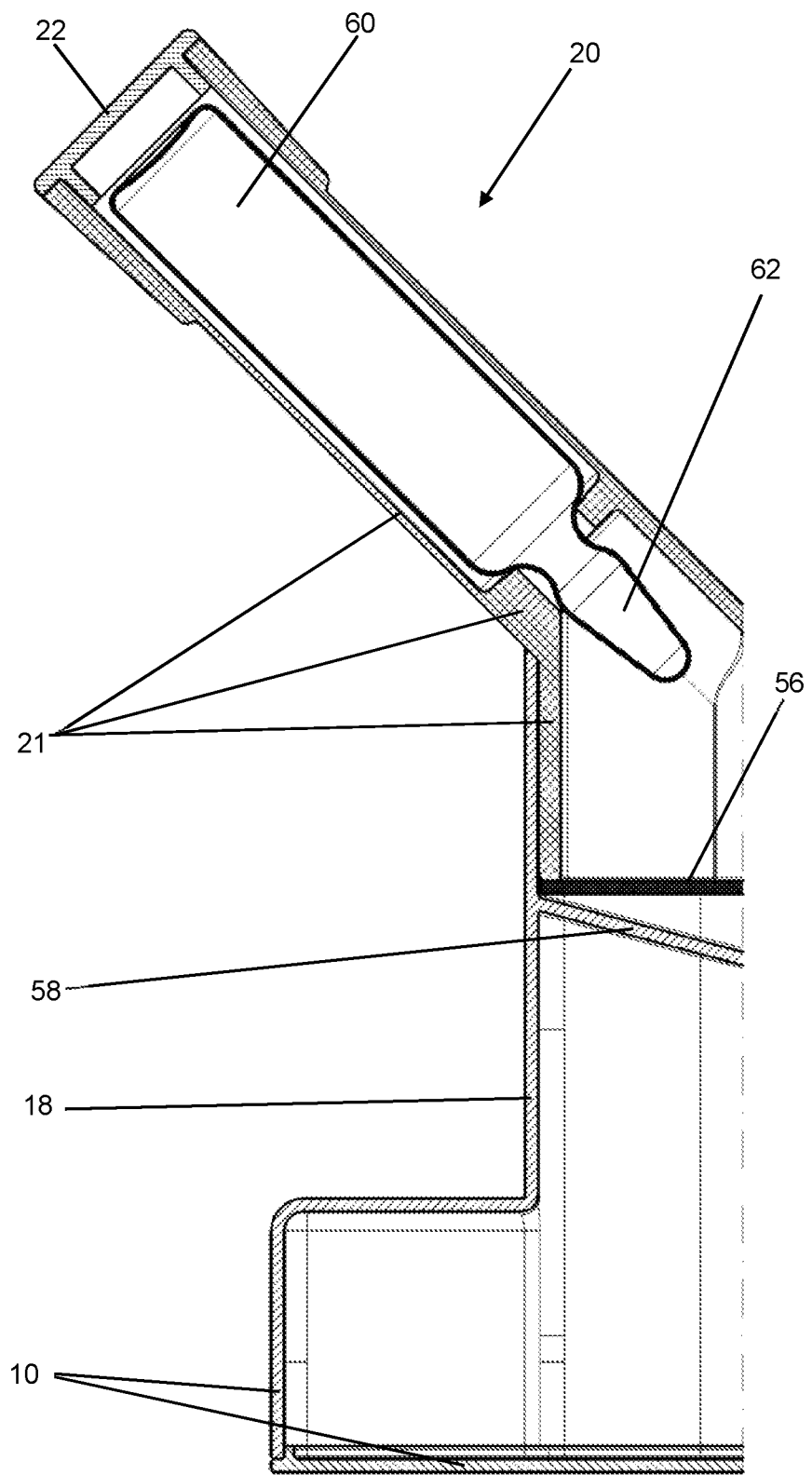
FIG. 4: shows a detail of the device according to FIGS. 1, 2, and 3 in a schematic cross-sectional view that corresponds to a section plane parallel to section plane AA according to FIG. 2.

FIGS. 1 to 4 shows schematic depictions of a first device according to the invention that is well-suited for implementing a method according to the invention. In this context, FIG. 1 shows a schematic perspective view of a device according to the invention as full-prepacked mixing system, FIG. 2 shows the device according to FIG. 1 in a frontal view with a section plane AA, FIG. 3 shows the device according to FIGS. 1 and 2 in a schematic cross-sectional view according to section plane AA according to FIG. 2, and FIG. 4 shows a detail of said device according to FIGS. 1, 2, and 3 in a schematic cross-sectional view corresponding to a section plane that is parallel to section plane AA according to FIG. 2.

The device comprises a cartridge 1 that contains a cement powder as starting component of the PMMA bone cement to be produced. The cartridge 1 is closed on the upper side (on the top in FIGS. 1 and 3) by means of a dispensing plunger 2. The dispensing plunger 2 can be locked against the walls of the cartridge 1. A mixing rod 4 is guided through a centric feed-through in the dispensing plunger 2 and can be pulled into and out of the cartridge 1 and is supported in the dispensing plunger 2, and thus in the cartridge 1, such that it can be rotated. A handle part 6 for manual operation of the mixing rod 4 is attached on the upper end of the mixing rod 4 (on the top in FIGS. 1, 2, and 3).

The cartridge 1 with the base 10 is attached in detachable manner in the area of a socket 8 on a base 10 of the device. An upper (outer) hollow cylinder 12 is arranged on the upper side of the base 10, whereby said cylinder and the base are provided as a single part. A rod 14 with a push-button 15 for operation of the rod 14 is guided through a feed-through in a cover plate 16. The cover plate 16 closes the upper hollow cylinder 12 in upward direction in pressure-tight manner. For this purpose, a sealing ring is provided in the feed-through for the rod 14 by means of which the rod 14 is sealed with respect to the feed-through. The dispensing plunger 2 has a vacuum connector provided in it to which a vacuum conduit 17 is connected that leads into the interior of the upper hollow cylinder 12. The vacuum connector can be used to evacuate the interior of the cartridge 1 and, theoretically, the vacuum connector can also be used to supply ethylene oxide for sterilisation of the content of the cartridge 1, when the vacuum conduit 17 is not connected to the vacuum connector and/or before the vacuum conduit 17 is connected to the vacuum connector.

Moreover, a connecting socket 18 is provided on the base 10 next to the hollow cylinder 12 and is part of a connector 24 of a monomer container 60 of the device. Aside from the connecting socket 18, the connector 20 for the monomer container 60 further comprises an elastic receptacle 21 for the monomer container 60 and a lid 22, by means of which the connector 20 for the monomer container 60 can be closed off with respect to the outside after the monomer container 60 was inserted. The monomer container 60 is arranged in the interior of the connector 20 and thus inside the device. The monomer container 60 is a glass ampoule that is filled with a monomer liquid as second component for the PMMA bone cement to be produced. The elastic receptacle 21 consists of rubber or another elastic plastic material.

Further details of the design of the device are evident from FIGS. 3 and 4. The interior of the cartridge 1 is formed by a cylindrical internal space 24 that contains the cement powder as first component. Moreover, the internal space 24 of the cartridge 1 has a mixing facility 26 consisting of multiple mixing vanes 26 arranged in it that is attached to the mixing rod 4 and can be moved in the internal space 24 of the cartridge 1 by means of the mixing rod 4. The dispensing plunger 2 has a two-part design and consists of a sterilisation plunger 28 (upper part of the dispensing plunger in FIG. 3) and a sealing plunger 30 (lower part of the dispensing plunger in FIG. 3) that is sealed with respect to the internal wall of the internal space 24 by means of a seal 29. The sealing plunger 30 comprises a gas-permeable, but powder-impermeable pore disc by means of which the internal space 24 can be evacuated. The dispensing plunger 2 has a cylindrical outer circumference and closes tightly against the walls of the internal space 24. The dispensing plunger 2 can be propelled in the internal space 24 in the direction of a dispensing opening on the floor of the internal space 24 of the cartridge 1 that is situated on the side of the internal space 24 of the cartridge 1 that is opposite to the dispensing plunger 2.

For connecting the cartridge 1 to the base 10, a base connector 34 having an external thread as the connection to the cartridge 1 is provided, in which a powder-impermeable and liquid-permeable filter 32 is arranged. A cartridge connector 36 having an internal thread matching the external thread of the base connector 34 is provided on the side of the internal space 24 of the cartridge 1 that is opposite to the dispensing plunger 2. The cartridge connector 36 bounds the dispensing opening of the cartridge 1. The cartridge connector 36 is screwed onto the base connector 34 and closes off tightly with respect to same.

A connecting conduit 38 connecting the hollow cylinder 12 to the internal space 24 of the cartridge 1 is provided between the hollow cylinder 12 and the internal space 24 of the cartridge 1. The filter 32 is arranged at the junction into the internal space 24 of the cartridge 1 and prevents cement powder from the internal space 24 of the cartridge 1 from entering the connecting conduit 38. The connecting conduit 38 forms a loop 40 with a high apex in order to prevent the monomer liquid from flowing uncontrolled through the connecting conduit 38 into the internal space 24 of the cartridge 1. A small viewing window (not shown) can be provided for visual inspection of the loop 40. For this purpose, the connecting conduit 38 must be transparent in the region of the loop 40.

The socket 8, base 10, and connecting socket 18 for the monomer container 60 are produced, as a single part, from a plastic material, for example by means of injection moulding. The connecting conduit 38 merges into a hollow space 41 in a lower hollow cylinder 42, whereby the lower (inner) hollow cylinder 42 has a smaller internal diameter than the upper (outer) hollow cylinder 12. The lower hollow cylinder 42 is bounded, on the underside (on the bottom in FIG. 3), by means of a funnel-shaped floor 43 that tapers steadily downwards. This ensures that the monomer liquid can flow and/or be pushed completely out of the lower hollow cylinder 42. The lower hollow cylinder 42 has a pumping plunger 44 arranged in it that fits on the inside and can be pressed and/or pushed into the interior of the lower hollow cylinder 42 in the direction of the funnel-shaped floor 43 (downwards in FIG. 3).

The pumping plunger 44 is formed by a hollow body made of a plastic material and is formed on the lower surface 45 as a negative image of the floor 43 of the lower hollow cylinder 42. The pumping plunger 44 is sealed with respect to the internal wall of the lower hollow cylinder 42 by means of a seal 53 and is supported such as to be mobile in longitudinal direction (downwards in FIG. 3) in the lower hollow cylinder 42.

An open hollow space 46, in which a vacuum plunger 47 is arranged such as to be axially mobile, is provided in the interior of the upper hollow cylinder 12. The vacuum plunger 47 is sealed with respect to the internal wall of the upper hollow cylinder 12 by means of a seal 48. As a result, the vacuum plunger 47 separates, in upward direction, an upper closed hollow space 49 that is bounded by the cover plate 16, the internal wall of the upper hollow cylinder 12, and by the vacuum plunger 47. In contrast, openings 50 are provided in the floor of the open lower hollow space 46. The upper closed hollow space 49 is connected to the vacuum conduit 17 by means of a connector 52. The vacuum plunger 47 is affixed to the pumping plunger 44. In the present embodiment, it is also feasible to provide the vacuum plunger 47 and the pumping plunger 44 in a one-part design.

A junction 54 of the connector 20 for the monomer container 60 into the lower hollow cylinder 42 and/or the hollow space 41 is provided on a jacket surface of the lower hollow cylinder 42, right below the lower surface 45 of the pumping plunger 44. The junction 54 forms a conduit means for the monomer liquid such that the junction 54 can be considered to be part of a connecting conduit 38, 40 for the monomer liquid, in which the lower hollow cylinder 42 is arranged.

The connector 20 for the monomer container 60 has a screen 56 or filter 56 arranged in it that can be used to trap fragments and parts of the opened monomer container 60. An inclined floor surface 58 that is inclined in the direction of the junction 54 is provided in the connecting socket 18 below the screen 56 and/or filter 56. As a result, all of the monomer liquid can flow from the monomer container 60 through the junction 54 into the lower hollow cylinder 42.

The monomer container 60 is a glass ampoule 60 with an ampoule head 62 that can be broken off and a neck that can be broken open, whereby the neck connects the ampoule head 62 to the body of the ampoule 60. Due to the elasticity of the receptacle 21 for the monomer container 60 and due to the receptacle 21 being thicker in the area of the neck, the head 62 of the monomer container 60 can be broken off by bending the receptacle 21 with the monomer container 60 in it. Accordingly, the receptacle 21 of appropriate shape, in particular being thicker in the area of the neck, forms an opening means 21 for opening the monomer container 60. Other opening means for shearing off the head 62 of the monomer container 60 can be implemented just as well.

A method according to the invention can be implemented with the device according to FIGS. 1 to 4, for example as follows. The base 10 of the device is placed on a table or any other fitting level support. The monomer container 60 is opened by kinking the elastic receptacle 21 by breaking off and/or breaking open the head 62. The monomer liquid from the monomer container 60 flows through the screen 54 and/or the filter 54, whereby fragments of the monomer container 60 are retained. The inclined floor surface 58 guides the monomer liquid through the junction 54 into the lower hollow cylinder 42 and/or the hollow space 41. The free hollow space 41 of the lower hollow cylinder 42 is getting filled completely with the monomer liquid, since the monomer container 60 contains more monomer liquid than the combination of the lower hollow cylinder 42 and/or the hollow space 41 and the connecting conduit 38 up to the loop 40 can take up. Enclosed air escapes through the junction 54 since the junction is situated at the highest point of the space bounded by the hollow cylinder 42, the floor 45 of the pumping plunger 44, and the connecting conduit 38 up to just below the loop 40. In this context, the monomer liquid cannot flow beyond the apex of the loop 40 since the apex is situated clearly above the junction 54 and, in addition, the apex is arranged above the liquid level of the monomer liquid in the connector 20 such that the monomer liquid will not rise this high without being exposed to a pressure.

Subsequently, a manual pressure is exerted in the direction of the base 10 by the user by means of the push-button 15 and thus by means of the rod 14. As a result, the vacuum plunger 47 is being pushed downwards in the hollow space 46 and the pumping plunger 44 is being pushed into the hollow cylinder 42 and/or the hollow space 41. The pumping plunger 44 can be pushed into the hollow cylinder 42 and/or the hollow space 41 either completely or partially in order to transfer and/or press the desired amount of monomer liquid from the hollow cylinder 42 through the connecting conduit 38 into the internal space 24 of the cartridge 1. The amount of monomer liquid that is pressed in can be adjusted by varying the depth to which the pumping plunger 44 is being pushed into the hollow cylinder 42. For this purpose, markings (not shown) can be provided on the outside of the rod 14. The monomer liquid is being pressed through the filter 32 into the internal space 24 of the cartridge 1, where it rises and mixes with the cement powder stored in the internal space 24 of the cartridge 1.

Concurrently, the motion of the vacuum plunger 47 enlarges the hollow space 49 between the vacuum plunger 47 and the cover plate 46 in the upper hollow cylinder 12. As a result, the gas pressure in the hollow space 49 decreases. The decrease in pressure is transmitted by means of the vacuum conduit 17 and the vacuum connector of the sealing plunger 30 as well as through the pore filter of the sterilisation plunger 28 into the internal space 24 of the cartridge 1. As a result, the internal space 24 of the cartridge 1 is being evacuated through the motion of the vacuum plunger 47 and/or of the plungers 44, 47. Since the vacuum plunger 47 has a larger diameter than the pumping plunger 44, the volume of monomer liquid that is pushed out of the hollow space 41 into the internal space 24 of the cartridge 1 is smaller than the amount of gas that is evacuated from the internal space of the cartridge 1 through the enlarging volume in the hollow space 49. Therefore, the pressure in the internal space of the cartridge 1 decreases when the vacuum plunger 47 and the pumping plunger 44 are being pushed in.

Once the desired amount of monomer liquid has been filled into the internal space 24 of the cartridge 1, the monomer liquid and the cement powder are being mixed by pushing-in, pulling-out and rotating the mixing facility 26 and/or the mixing rod 4 by means of the handle part 6, and the cement dough and/or the PMMA bone cement is thus being mixed. After the mixing is completed, the mixing rod 4 is pulled out of the internal space 24 of the cartridge 1 up to the limit stop and broken off to make sure that it does not interfere later on. If applicable, a locking mechanism of the dispensing plunger 2 can be detached. Subsequently, the vacuum conduit 17 is disconnected from the vacuum connector of the sealing plunger 30 and the cartridge 1 is unscrewed from the base 10. A dispensing tube (not shown) can be screwed onto the internal thread on the cartridge connector 36. Subsequently, the ready-mixed bone cement can be expelled from the internal space 24 of the cartridge 1 through the dispensing opening and the dispensing tube by pressing the dispensing plunger 2 inwards, and the ready-mixed bone cement can be applied.

Figure 5:
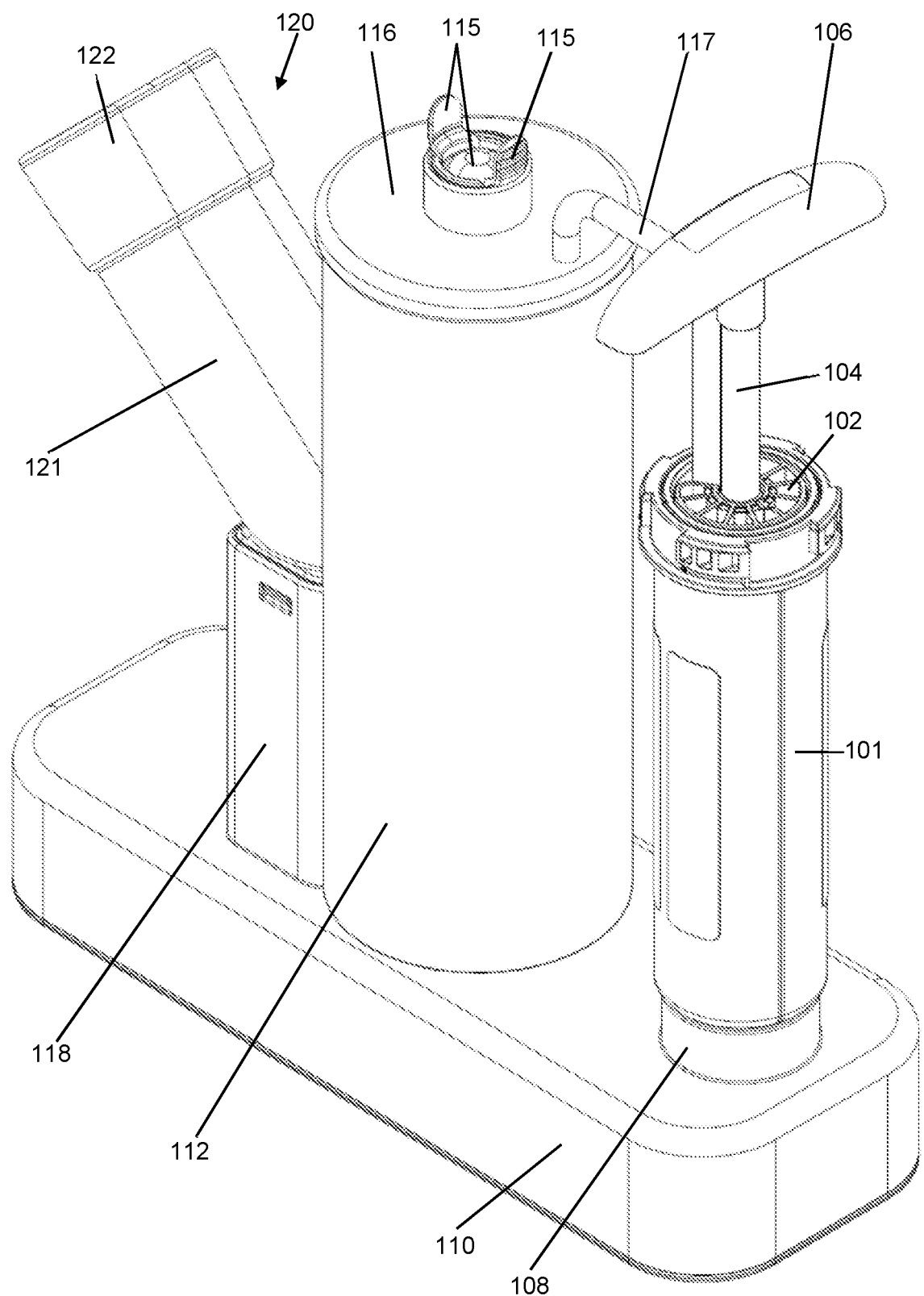
FIG. 5: shows a schematic perspective view of an alternative second device according to the invention as full-prepacked mixing system.
Figure 6:
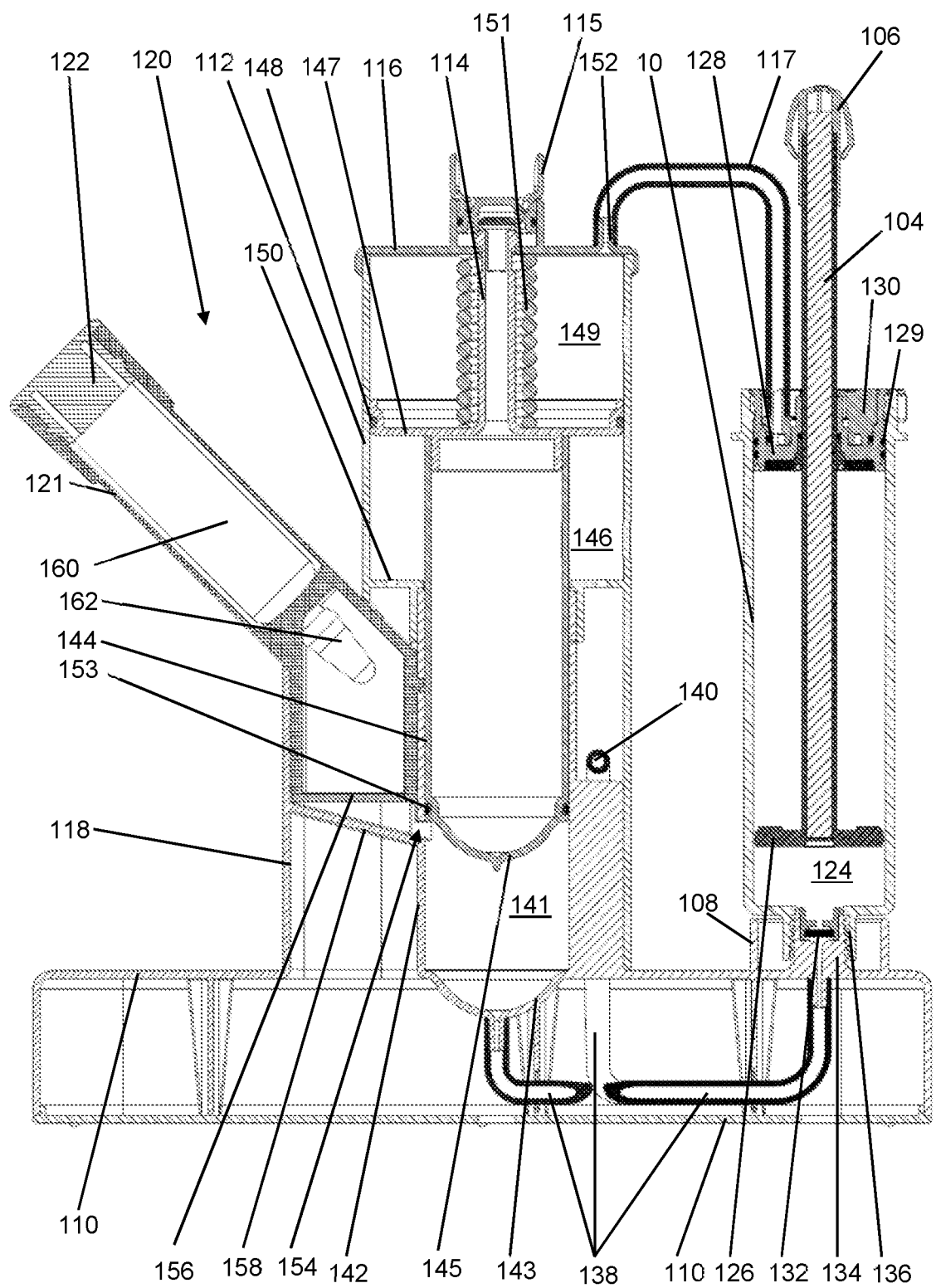
FIG. 6: shows the device according to FIG. 5 in a schematic cross-sectional view.

FIGS. 5 and 6 show schematic depictions of a second alternative device according to the invention that is well-suited for implementing a method according to the invention. In this context, FIG. 5 shows a schematic perspective view of the alternative device according to the invention as full-prepacked mixing system, and FIG. 6 shows the device according to FIG. 5 in a schematic cross-sectional view.

The device comprises a cartridge 101 that contains a cement powder as starting component of the PMMA bone cement to be produced. The cartridge 101 is closed on the upper side (on the top in FIGS. 5 and 6) by means of a dispensing plunger 102. The dispensing plunger 102 can be locked against the walls of the cartridge 101. A mixing rod 104 is guided through a centric feed-through in the dispensing plunger 102 and can be pulled into and out of the cartridge 101 and is supported in the dispensing plunger 102, and thus in the cartridge 101, such that it can be rotated. A handle part 106 for manual operation of the mixing rod 104 is attached on the upper end of the mixing rod 104 (on the top in FIGS. 5 and 6).

The cartridge 101 with the base 110 is attached in detachable manner in the area of a socket 108 on a base 110 of the device. An upper (outer) hollow cylinder 112 is arranged on the upper side of the base 110, whereby said cylinder and the base are provided as a single part. A locked-in rod 114 with a securing mechanism 115 for unlocking the rod 114 and/or for triggering the device is guided through a feed-through in a cover plate 116. The cover plate 116 closes the upper hollow cylinder 112 in upward direction in pressure-tight manner. For this purpose, a sealing ring is provided in a seat of the securing mechanism 115 by means of which the securing mechanism 115 is sealed with respect to the seat.

The dispensing plunger 102 has a vacuum connector provided in it to which a vacuum conduit 117 is connected that leads into the interior of the upper hollow cylinder 112. The vacuum connector can be used to evacuate the interior of the cartridge 101 and, theoretically, the vacuum connector can also be used to supply ethylene oxide for sterilisation of the content of the cartridge 101, when the vacuum conduit 117 is not connected to the vacuum connector and/or before the vacuum conduit 117 is connected to the vacuum connector.

Moreover, a connecting socket 118 is provided on the base 110 next to the hollow cylinder 112 and is part of a connector 120 for a monomer container 160 of the device. Aside from the connecting socket 118, the connector 120 for the monomer container 160 further comprises an elastic receptacle 121 for the monomer container 160 and a lid 122, by means of which the connector 120 for the monomer container 160 can be closed off with respect to the outside after the monomer container 160 was inserted. The monomer container 160 is arranged in the interior of the connector 120 and thus inside the device. The monomer container 160 is a glass ampoule that is filled with a monomer liquid as second component for the PMMA bone cement to be produced. The elastic receptacle 121 consists of rubber or another elastic plastic material.

Further details of the design of the device are evident from FIG. 6. The interior of the cartridge 101 is formed by a cylindrical internal space 124 that contains the cement powder as first component. Moreover, the internal space 124 of the cartridge 101 has a mixing facility 126 consisting of multiple mixing vanes 126 arranged in it that is attached to the mixing rod 104 and can be moved in the internal space 124 of the cartridge 101 by means of the mixing rod 104. The dispensing plunger 102 has a two-part design and consists of a sterilisation plunger 128 (upper part of the dispensing plunger in FIG. 6) and a sealing plunger 130 (lower part of the dispensing plunger in FIG. 6) that is sealed with respect to the internal wall of the internal space 124 by means of a seal 129. The sealing plunger 130 comprises a gas-permeable, but powder-impermeable pore disc by means of which the internal space 124 can be evacuated. The dispensing plunger 102 has a cylindrical outer circumference and closes tightly against the walls of the internal space 124. The dispensing plunger 102 can be propelled in the internal space 124 in the direction of a dispensing opening on the floor of the internal space 124 of the cartridge 101 that is situated on the side of the internal space 124 of the cartridge 101 that is opposite to the dispensing plunger 102.

For connecting the cartridge 101 to the base 110, a base connector 134 having an external thread as the connection to the cartridge 101 is provided, in which a powder-impermeable and liquid-permeable filter 132 is arranged. A cartridge connector 136 having an internal thread matching the external thread of the base connector 134 is provided on the side of the internal space 124 of the cartridge 101 that is opposite to the dispensing plunger 102. The cartridge connector 136 bounds the dispensing opening of the cartridge 101. The cartridge connector 136 is screwed onto the base connector 134 and closes off tightly with respect to same.

A connecting conduit 138 connecting the hollow cylinder 112 to the internal space 124 of the cartridge 101 is provided between the hollow cylinder 112 and the internal space 124 of the cartridge 101. The filter 132 is arranged at the junction into the internal space 124 of the cartridge 101 and prevents cement powder from the internal space 124 of the cartridge 101 from entering the connecting conduit 138. The connecting conduit 138 forms a loop 140 with a high apex in order to prevent the monomer liquid from flowing uncontrolled through the connecting conduit 138 into the internal space 124 of the cartridge 101. A small viewing window (not shown) can be provided for visual inspection of the loop 140. For this purpose, the connecting conduit 138 must be transparent in the region of the loop 140.

The socket 108, base 110, and connecting socket 118 for the monomer container 160 are produced, as a single part, from a plastic material, for example by means of injection moulding. The connecting conduit 138 merges into a hollow space 141 in a lower hollow cylinder 142, whereby the lower (inner) hollow cylinder 142 has a smaller internal diameter than the upper (outer) hollow cylinder 112. The lower hollow cylinder 142 is bounded, on the underside (on the bottom in FIG. 6), by means of a funnel-shaped floor 143 that tapers steadily downwards. This ensures that the monomer liquid can flow and/or be pushed completely out of the lower hollow cylinder 142. The lower hollow cylinder 142 has a pumping plunger 144 arranged in it that fits on the inside and can be pressed and/or pushed into the interior of the lower hollow cylinder 142 in the direction of the funnel-shaped floor 143 (downwards in FIG. 6).

The pumping plunger 144 is formed by a hollow body made of a plastic material and is formed on the lower surface 145 as a negative image of the floor 143 of the lower hollow cylinder 142. The pumping plunger 144 is sealed with respect to the internal wall of the lower hollow cylinder 142 by means of a seal 153 and is supported such as to be mobile in longitudinal direction (downwards in FIG. 6) in the lower hollow cylinder 142.

An open hollow space 146, in which a vacuum plunger 147 is arranged such as to be axially mobile, is provided in the interior of the upper hollow cylinder 112. The vacuum plunger 147 is sealed with respect to the internal wall of the upper hollow cylinder 112 by means of a seal 148. As a result, the vacuum plunger 147 separates, in upward direction, an upper closed hollow space 149 that is bounded by the cover plate 116, the internal wall of the upper hollow cylinder 112, the securing mechanism 115, and by the vacuum plunger 147. In contrast, openings 150 are provided in the floor of the open lower hollow space 146. A tensioned compression spring 151 arranged to surround the rod 114 is provided in the interior of the hollow space 149 of the upper hollow cylinder 112. The tension of the compression spring 151 is maintained by the rod 114 between the cover plate 116 and the upper side of the vacuum plunger 147 that is locked by means of the cover plate 116. The upper closed hollow space 149 is connected to the vacuum conduit 117 by means of a connector 152. The vacuum plunger 147 is affixed to the pumping plunger 144. In the present embodiment, it is also feasible to provide the vacuum plunger 147 and the pumping plunger 144 in a one-part design.

A junction 154 of the connector 120 for the monomer container 160 into the lower hollow cylinder 142 and/or the hollow space 141 is provided on a jacket surface of the lower hollow cylinder 142, right below the lower surface 145 of the pumping plunger 144. The junction 154 forms a conduit means for the monomer liquid such that the junction 154 can be considered to be part of a connecting conduit 138, 140 for the monomer liquid, in which the lower hollow cylinder 142 is arranged.

The connector 120 for the monomer container 160 has a screen 156 or filter 156 arranged in it that can be used to trap fragments and parts of the opened monomer container 160. An inclined floor surface 158 that is inclined in the direction of the junction 154 is provided in the connecting socket 118 below the screen 156 and/or filter 156. As a result, all of the monomer liquid can flow from the monomer container 160 through the junction 154 into the lower hollow cylinder 142.

The monomer container 160 is a glass ampoule 160 with an ampoule head 162 that can be broken off and a neck that can be broken open, whereby the neck connects the ampoule head 162 to the body of the ampoule 160. Due to the elasticity of the receptacle 121 for the monomer container 160 and due to the receptacle 121 being thicker in the area of the neck, the head 162 of the monomer container 160 can be broken off by bending the receptacle 121 with the monomer container 160 in it. Accordingly, the receptacle 121 of appropriate shape, in particular being thicker in the area of the neck, forms an opening means 121 for opening the monomer container 160. Other opening means for shearing off the head 162 of the monomer container 160 can be implemented just as well.

A method according to the invention can be implemented with the alternative second device according to FIGS. 5 and 6, for example as follows. The base 110 of the device is placed on a table or any other fitting level support. The monomer container 160 is opened by kinking the elastic receptacle 121 by breaking off and/or breaking open the head 162. The monomer liquid from the monomer container 160 flows through the screen 156 and/or the filter 156, whereby fragments of the monomer container 160 are retained. The inclined floor surface 158 guides the monomer liquid through the junction 154 into the lower hollow cylinder 142 and/or the hollow space 141. The free hollow space 141 of the lower hollow cylinder 142 is getting filled completely with the monomer liquid, since the monomer container 160 contains more monomer liquid than the combination of the lower hollow cylinder 142 and/or the hollow space 141 and the connecting conduit 138 up to the loop 140 can take up. Enclosed air escapes through the junction 154 since the junction is situated at the highest point of the space bounded by the hollow cylinder 142, the floor 145 of the pumping plunger 144, and the connecting conduit 138 up to just below the loop 140. In this context, the monomer liquid cannot flow beyond the apex of the loop 140 since the apex is situated clearly above the junction 154 and, in addition, the apex is arranged above the liquid level of the monomer liquid in the connector 120 such that the monomer liquid will not rise this high without being exposed to a pressure.

The securing mechanism 115 can be pushed downward into the seat by compressing two flat handle levers that are arranged on the securing mechanism 115 and project out of the seat in the cover plate 116. As a result, the securing mechanism 115 slides onto the upper end of the rod 114 and multiple snap-in hooks that are arranged on the upper end of the rod 114 become deformed. As a result, the rod 114 is rendered freely mobile and the rod 114 is accelerated instantaneously, together with the vacuum plunger 147 and the pumping plunger 144, in the direction of the base 110 by the tensioned compression spring 155.

The compression spring 151 pushes the vacuum plunger 147 downwards in the hollow space 146. The monomer liquid from the hollow space 141 is pressed through the connecting conduit 138 and the filter 132 into the internal space 124 of the cartridge 101, where it rises and mixes with the cement powder stored in the internal space 124 of the cartridge 101.

Concurrently, the motion of the vacuum plunger 147 enlarges the hollow space 149 between the vacuum plunger 147 and the cover plate 146 in the upper hollow cylinder 112. As a result, the gas pressure in the hollow space 149 decreases. The decrease in pressure is transmitted by means of the vacuum conduit 117 and the vacuum connector of the sealing plunger 130 as well as through the pore filter of the sterilisation plunger 128 into the internal space 124 of the cartridge 101. As a result, the internal space 124 of the cartridge 101 is being evacuated through the motion of the vacuum plunger 147 and/or of the plungers 144, 147. Since the vacuum plunger 147 has a larger diameter than the pumping plunger 144, the volume of monomer liquid that is pushed out of the hollow space 141 into the internal space 124 of the cartridge 101 is smaller than the amount of gas that is evacuated from the internal space of the cartridge 101 through the enlarging volume in the hollow space 149. Therefore, the pressure in the internal space of the cartridge 101 decreases when the vacuum plunger 147 and the pumping plunger 144 are being pushed in.

Once the desired amount of monomer liquid has been filled into the internal space 124 of the cartridge 101, the monomer liquid and the cement powder are being mixed by pushing-in, pulling-out and rotating the mixing facility 126 and/or the mixing rod 104 by means of the handle part 6, and the cement dough and/or the PMMA bone cement is thus being mixed. After the mixing is completed, the mixing rod 104 is pulled out of the internal space 124 of the cartridge 101 up to the limit stop and broken off to make sure that it does not interfere later on. If applicable, a locking mechanism of the dispensing plunger 102 can be detached. Subsequently, the vacuum conduit 117 is disconnected from the vacuum connector of the sealing plunger 130 and the cartridge 101 is unscrewed from the base 110. A dispensing tube (not shown) can be screwed onto the internal thread on the cartridge connector 136. Subsequently, the ready-mixed bone cement can be expelled from the internal space 124 of the cartridge 101 through the dispensing opening and the dispensing tube by pressing the dispensing plunger 102 inwards, and the ready-mixed bone cement can be applied.

Figure 7:
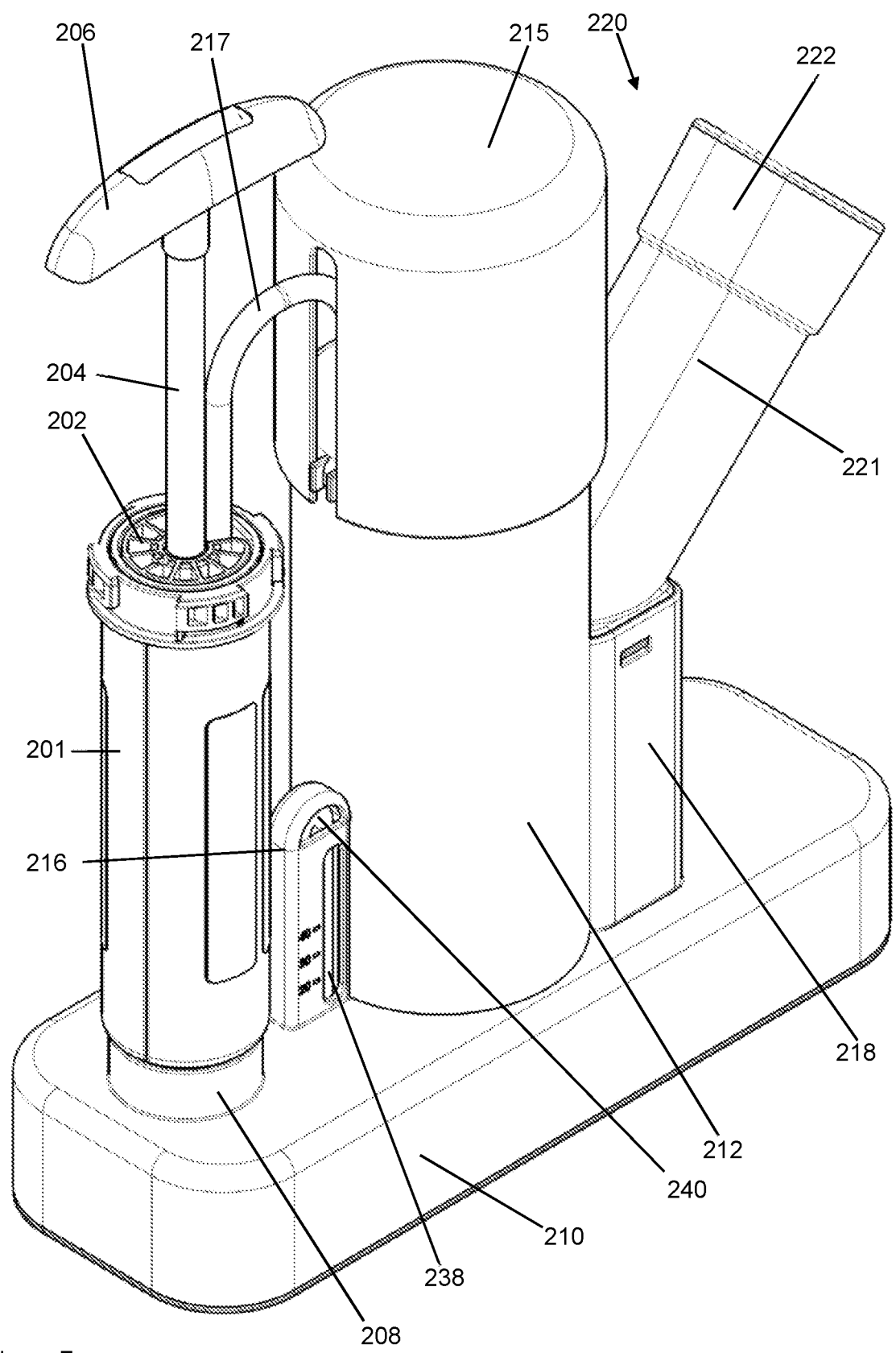
FIG. 7: shows a schematic perspective view of an alternative third device according to the invention as full-prepacked mixing system.
Figure 8:
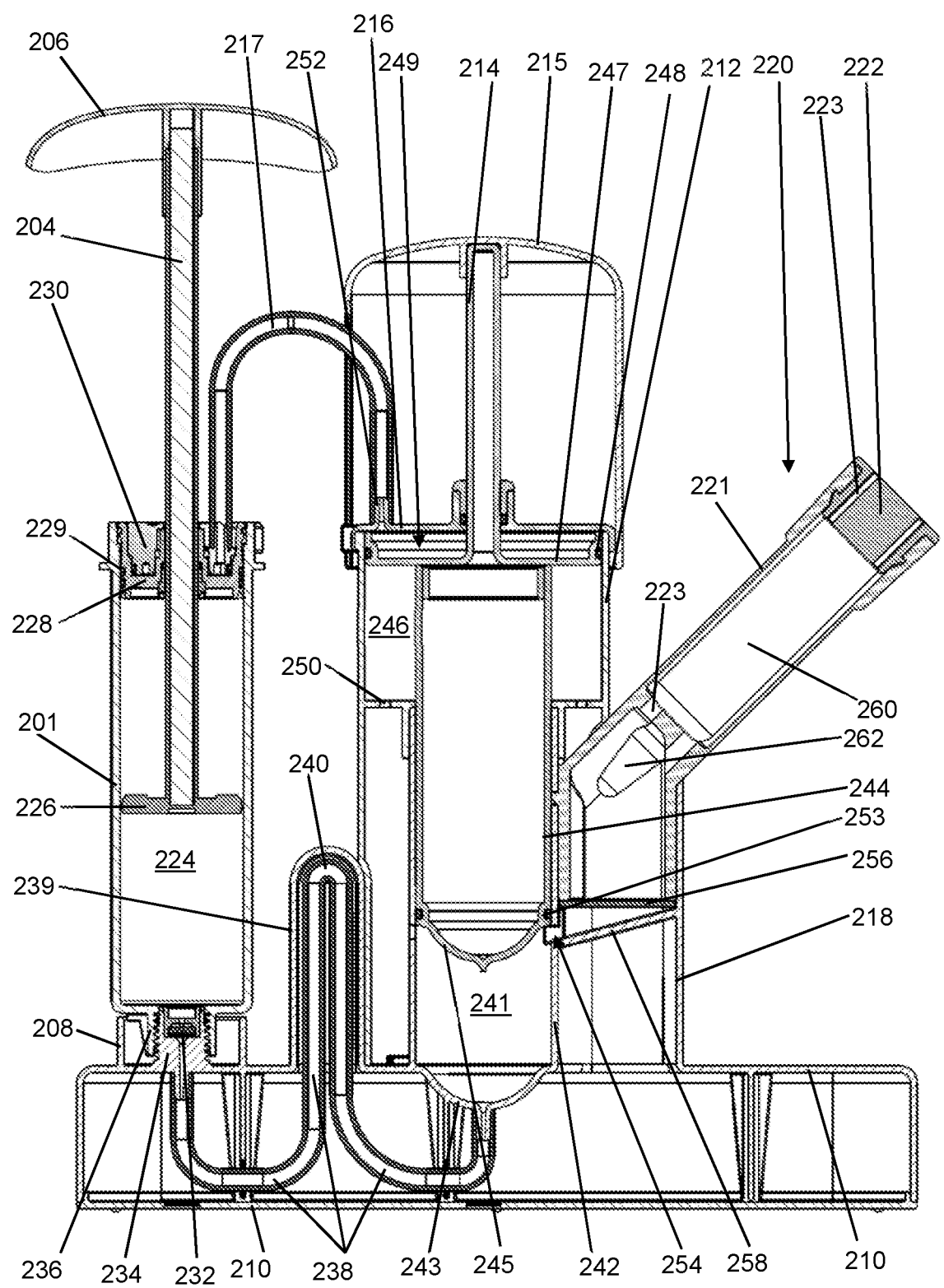
FIG. 8: shows the device according to FIG. 7 in a schematic cross-sectional view.

FIGS. 7 and 8 show schematic depictions of a third alternative device according to the invention that is well-suited for implementing a method according to the invention. In this context, FIG. 7 shows a schematic perspective view of the alternative device according to the invention as full-prepacked mixing system, and FIG. 8 shows the device according to FIG. 7 in a schematic cross-sectional view.

The third alternative device has a similar design as the first device according to FIGS. 1 to 4 and the second alternative device according to FIGS. 5 and 6 and comprises a cartridge 201 that contains a cement powder as first starting component of the PMMA bone cement to be produced. The cartridge 201 is closed on the upper side (on the top in FIGS. 7 and 8) by means of a dispensing plunger 202. The dispensing plunger 202 can be locked against the walls of the cartridge 201. A mixing rod 204 is guided through a centric feed-through in the dispensing plunger 202 and can be pulled into and out of the cartridge 201 and is supported in the dispensing plunger 202, and thus in the cartridge 201, such that it can be rotated. A handle part 206 for manual operation of the mixing rod 204 is attached on the upper end of the mixing rod 204 (on the top in FIGS. 7 and 8).

The cartridge 201 with the base 210 is attached in detachable manner in the area of a socket 208 on a base 210 of the device. An upper (outer) hollow cylinder 212 is arranged on the upper side of the base 210, whereby said cylinder and the base are provided as a single part. A rod 214 with a hood 215 for operation of the rod 214 is guided through a feed-through in a cover plate 216. The cover plate 216 closes the upper hollow cylinder 212 in upward direction in pressure-tight manner. For this purpose, a sealing ring is provided in the feed-through for the rod 214 by means of which the rod 214 is sealed with respect to the feed-through.

The dispensing plunger 202 has a vacuum connector provided in it to which a vacuum conduit 217 is connected that leads into the interior of the upper hollow cylinder 212. The vacuum connector can be used to evacuate the interior of the cartridge 201 and, theoretically, the vacuum connector can also be used to supply ethylene oxide for sterilisation of the content of the cartridge 201, when the vacuum conduit 217 is not connected to the vacuum connector and/or before the vacuum conduit 217 is connected to the vacuum connector.

Moreover, a connecting socket 218 is provided on the base 210 next to the hollow cylinder 212 and is part of a connector 220 for a monomer container 260 of the device. Aside from the connecting socket 218, the connector 220 for the monomer container 260 further comprises an elastic receptacle 221 for the monomer container 260 and a lid 222, by means of which the connector 220 for the monomer container 260 can be closed off with respect to the outside after the monomer container 260 was inserted. The monomer container 260 is arranged in the interior of the connector 220 and thus inside the device. The monomer container 260 is a glass ampoule that is filled with a monomer liquid as second component for the PMMA bone cement to be produced. The elastic receptacle 221 consists of rubber or another elastic plastic material. Multiple ventilation passages 223 are arranged in the lid 222 and in the thickened part of the receptacle 220. The purpose of the ventilation passages 223 is to allow the monomer liquid to readily flow out of the opened ampoule 260 and/or the opened monomer container 260. In this context, the ventilation passages 223 prevent a negative pressure from being generated in the area of the lid 222 of the monomer container 220 that would counteract the flow of the monomer liquid.

Further details of the design of the device are evident from FIG. 8. The interior of the cartridge 201 is formed by a cylindrical internal space 224 that contains the cement powder as first component. Moreover, the internal space 224 of the cartridge 201 has a mixing facility 226 consisting of multiple mixing vanes 226 arranged in it that is attached to the mixing rod 204 and can be moved in the internal space 224 of the cartridge 201 by means of the mixing rod 204. The dispensing plunger 202 has a two-part design and consists of a sterilisation plunger 228 (upper part of the dispensing plunger in FIG. 8) and a sealing plunger 230 (lower part of the dispensing plunger in FIG. 8) that is sealed with respect to the internal wall of the internal space 224 by means of a seal 229. The sealing plunger 230 comprises a gas-permeable, but powder-impermeable pore disc by means of which the internal space 224 can be evacuated. The dispensing plunger 202 has a cylindrical outer circumference and closes tightly against the walls of the internal space 224. The dispensing plunger 202 can be propelled in the internal space 224 in the direction of a dispensing opening on the floor of the internal space 224 of the cartridge 201 that is situated on the side of the internal space 224 of the cartridge 201 that is opposite to the dispensing plunger 202.

For connecting the cartridge 201 to the base 210, a base connector 234 having an external thread as the connection to the cartridge 201 is provided, in which a powder-impermeable and liquid-permeable filter 232 is arranged. A cartridge connector 236 having an internal thread matching the external thread of the base connector 234 is provided on the side of the internal space 224 of the cartridge 201 that is opposite to the dispensing plunger 202. The cartridge connector 236 bounds the dispensing opening of the cartridge 201. The cartridge connector 236 is screwed onto the base connector 234 and closes off tightly with respect to same.

A connecting conduit 238 connecting the hollow cylinder 212 to the internal space 224 of the cartridge 201 is provided between the hollow cylinder 212 and the internal space 224 of the cartridge 201. The filter 232 is arranged at the junction into the internal space 224 of the cartridge 201 and prevents cement powder from the internal space 224 of the cartridge 201 from entering the connecting conduit 238. The connecting conduit 238 is guided, in part, in a housing 239 that contains viewing windows. The connecting conduit 238 forms a loop 240 with a high apex in the housing 239 in order to prevent the monomer liquid from flowing uncontrolled through the connecting conduit 238 into the internal space 224 of the cartridge 201. The viewing windows in the housing 239 are provided for visual control of the loop 240. Moreover, they allow the liquid level of the monomer liquid in the connecting conduit 238 to be determined. A scale is attached at one of the viewing windows for this purpose. To be able to see the liquid level, the connecting conduit 238 must be transparent in the region of the loop 240.

The socket 208, base 210, housing 239, and connecting socket 218 for the monomer container 260 are produced, as a single part, from a plastic material, for example by means of injection moulding. The connecting conduit 238 merges into a hollow space 241 in a lower hollow cylinder 242, whereby the lower (inner) hollow cylinder 242 has a smaller internal diameter than the upper (outer) hollow cylinder 212. The lower hollow cylinder 242 is bounded, on the underside (on the bottom in FIG. 8), by means of a funnel-shaped floor 243 that tapers steadily downwards. This ensures that the monomer liquid can flow and/or be pushed completely out of the lower hollow cylinder 242. The lower hollow cylinder 242 has a pumping plunger 244 arranged in it that fits on the inside and can be pressed and/or pushed into the interior of the lower hollow cylinder 242 in the direction of the funnel-shaped floor 243 (downwards in FIG. 8).

The pumping plunger 244 is formed by a hollow body made of a plastic material and is formed on the lower surface 245 as a negative image of the floor 243 of the lower hollow cylinder 242. The pumping plunger 244 is sealed with respect to the internal wall of the lower hollow cylinder 242 by means of a seal 253 and is supported such as to be mobile in longitudinal direction (downwards in FIG. 8) in the lower hollow cylinder 242.

An open hollow space 246, in which a vacuum plunger 247 is arranged such as to be axially mobile, is provided in the interior of the upper hollow cylinder 212. The vacuum plunger 247 is sealed with respect to the internal wall of the upper hollow cylinder 212 by means of a seal 248. As a result, the vacuum plunger 247 separates, in upward direction, an upper closed hollow space 249 that is bounded by the cover plate 216, the internal wall of the upper hollow cylinder 212, the securing mechanism 215, and by the vacuum plunger 247. In contrast, openings 250 are provided in the floor of the open lower hollow space 246. The upper closed hollow space 249 is connected to the vacuum conduit 217 by means of a connector 252. A vertical slit through which the flexible vacuum conduit 217 is guided is provided in the hood 215. When the hood 215 is pushed downward in the direction of the base 210, the vacuum conduit 217 slides in said slit. The vacuum plunger 247 is affixed to the pumping plunger 244. In the present embodiment, it is also feasible to provide the vacuum plunger 247 and the pumping plunger 244 in a one-part design.

A junction 254 of the connector 220 for the monomer container 260 into the lower hollow cylinder 242 and/or the hollow space 241 is provided on a jacket surface of the lower hollow cylinder 242, right below the lower surface 245 of the pumping plunger 244. The junction 254 forms a conduit means for the monomer liquid such that the junction 254 can be considered to be part of a connecting conduit 238, 240 for the monomer liquid, in which the lower hollow cylinder 242 is arranged.

The connector 220 for the monomer container 260 has a screen 256 or filter 256 arranged in it that can be used to trap fragments and parts of the opened monomer container 260. An inclined floor surface 258 that is inclined in the direction of the junction 254 is provided in the connecting socket 218 below the screen 256 and/or filter 256. As a result, all of the monomer liquid can flow from the monomer container 260 through the junction 254 into the lower hollow cylinder 242.

The monomer container 260 is a glass ampoule 260 with an ampoule head 262 that can be broken off and a neck that can be broken open, whereby the neck connects the ampoule head 262 to the body of the ampoule 260. Due to the elasticity of the receptacle 221 for the monomer container 260 and due to the receptacle 221 being thicker in the area of the neck, the head 262 of the monomer container 260 can be broken off by bending the receptacle 221 with the monomer container 260 in it. Accordingly, the receptacle 221 of appropriate shape, in particular being thicker in the area of the neck, forms an opening means 221 for opening the monomer container 260. Other opening means for shearing off the head 262 of the monomer container 260 can be implemented just as well.

A method according to the invention can be implemented with the alternative second device according to FIGS. 7 and 8, for example as follows. The base 210 of the device is placed on a table or any other fitting level support. The monomer container 260 is opened by kinking the elastic receptacle 221 by breaking off and/or breaking open the head 262. The monomer liquid from the monomer container 260 flows through the screen 256 and/or the filter 256, whereby fragments of the monomer container 260 are retained. The inclined floor surface 258 guides the monomer liquid through the junction 254 into the lower hollow cylinder 242 and/or the hollow space 241. The ventilation passages 223 allow air from outside to flow along such that the monomer liquid can readily flow into the hollow space 241. The free hollow space 241 of the lower hollow cylinder 242 is getting filled completely with the monomer liquid, since the monomer container 260 contains more monomer liquid than the combination of the lower hollow cylinder 242 and/or the hollow space 241 and the connecting conduit 238 up to the loop 240 can take up. Enclosed air escapes through the junction 254 since the junction is situated at the highest point of the space bounded by the hollow cylinder 242, the floor 245 of the pumping plunger 244, and the connecting conduit 238 up to just below the loop 240. In this context, the monomer liquid cannot flow beyond the apex of the loop 240 since the apex is situated clearly above the junction 254 and, in addition, the apex is arranged above the liquid level of the monomer liquid in the connector 220 such that the monomer liquid will not rise this high without being exposed to a pressure.

Subsequently, a manual pressure is exerted in the direction of the base 210 by the user by means of the hood 215 and thus by means of the rod 214. As a result, the vacuum plunger 247 is being pushed downwards in the hollow space 246 and the pumping plunger 244 is being pushed into the hollow cylinder 242 and/or the hollow space 241. The pumping plunger 244 can be pushed into the hollow cylinder 242 and/or the hollow space 241 either completely or partially in order to transfer and/or press the desired amount of monomer liquid from the hollow cylinder 242 through the connecting conduit 238 into the internal space 224 of the cartridge 201. In this context, the transition of the monomer liquid and the liquid level of the monomer liquid in the hollow space 241 can be controlled by means of the viewing windows and the scale in the housing 239. The amount of monomer liquid that is pressed in can be adjusted by varying the depth to which the pumping plunger 244 is being pushed into the hollow cylinder 242. For this purpose, markings (not shown) can be provided on the outside of the hood 215. The monomer liquid is being pressed through the filter 232 into the internal space 224 of the cartridge 201, where it rises and mixes with the cement powder stored in the internal space 224 of the cartridge 201.

Concurrently, the motion of the vacuum plunger 247 enlarges the hollow space 249 between the vacuum plunger 247 and the cover plate 246 in the upper hollow cylinder 212. As a result, the gas pressure in the hollow space 249 decreases. The decrease in pressure is transmitted by means of the vacuum conduit 217 and the vacuum connector of the sealing plunger 230 as well as through the pore filter of the sterilisation plunger 228 into the internal space 224 of the cartridge 201. As a result, the internal space 224 of the cartridge 201 is being evacuated through the motion of the vacuum plunger 247 and/or of the plungers 244, 247. Since the vacuum plunger 247 has a larger diameter than the pumping plunger 244, the volume of monomer liquid that is pushed out of the hollow space 241 into the internal space 224 of the cartridge 201 is smaller than the amount of gas that is evacuated from the internal space of the cartridge 201 through the enlarging volume in the hollow space 249. Therefore, the pressure in the internal space of the cartridge 201 decreases when the vacuum plunger 247 and the pumping plunger 244 are being pushed in.

Once the desired amount of monomer liquid has been filled into the internal space 224 of the cartridge 201, the monomer liquid and the cement powder are being mixed by pushing-in, pulling-out and rotating the mixing facility 226 and/or the mixing rod 204 by means of the handle part 206, and the cement dough and/or the PMMA bone cement is thus being mixed. After the mixing is completed, the mixing rod 204 is pulled out of the internal space 224 of the cartridge 201 up to the limit stop and broken off to make sure that it does not interfere later on. If applicable, a locking mechanism of the dispensing plunger 202 can be detached. Subsequently, the vacuum conduit 217 is disconnected from the vacuum connector of the sealing plunger 230 and the cartridge 201 is unscrewed from the base 210. A dispensing tube (not shown) can be screwed onto the internal thread on the cartridge connector 236. Subsequently, the ready-mixed bone cement can be expelled from the internal space 224 of the cartridge 201 through the dispensing opening and the dispensing tube by pressing the dispensing plunger 202 inwards, and the ready-mixed bone cement can be applied.

Figure 9:
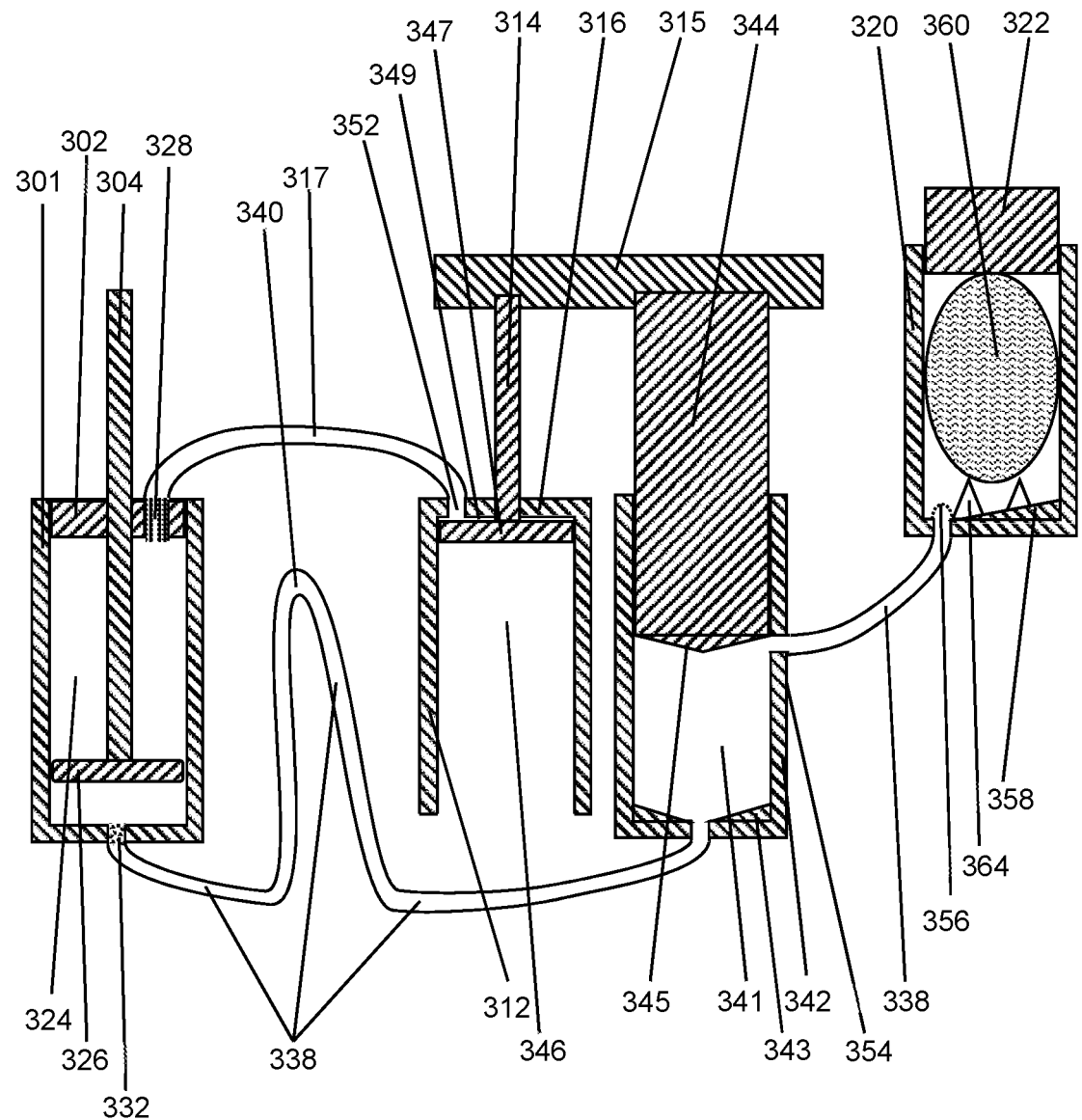
FIG. 9: shows a schematic cross-sectional view of an alternative fourth device according to the invention as full-prepacked mixing system, in which the schematic functional principle of the device is shown.

FIG. 9 shows a schematic cross-sectional view of an alternative fourth device according to the invention as full-prepacked mixing system, in which the schematic functional principle of the device is shown. It is self-evident that the parts of the fourth device according to the invention are connected to each other, in some case are connected to each other in detachable manner. Accordingly, the basic design can be presumed to be largely analogous to that of the three previous exemplary embodiments according to FIGS. 1 to 8.

The device comprises a cartridge 301 (on the left in FIG. 9) with an internal space 324 that contains a cement powder as first starting component for the production of the bone cement. The cartridge 301 is closed on the upper side by means of a dispensing plunger 302 that is axially mobile in the cartridge 301. A mixing rod 304, which is guided through the dispensing plunger 302 such as to be mobile, is connected to a mixing facility 326 in the internal space 324 of the cartridge 301.

The device further comprises a first hollow cylinder 342 and a second hollow cylinder 312, which, unlike the previous exemplary embodiments, are arranged separate with respect to each other and/or adjoining each other. A hollow space 341 and a pumping plunger 344 that is mobile in the hollow space 341 are provided in the first hollow cylinder 342. The pumping plunger 344 comprises a lower surface 345 that fits the funnel-shaped inclined floor 343 of the hollow space 341. The centre of the funnel-shaped floor 343 has a drain provided on it to which a connecting conduit 338 is connected that connects the hollow space 341 for the pumping plunger 344 to the internal space 324 of the cartridge 301 on the underside thereof. A powder-impermeable and liquid-permeable filter 332 is provided in this connection as well. In analogy to the previous exemplary embodiments, the connecting conduit 338 comprises a loop 340 at a fitting height.

The second hollow cylinder 312 is intended for generating a negative pressure. For this purpose, an axially mobile vacuum plunger 347 is arranged in the hollow space 341, which is open on its lower side, of the hollow cylinder 312, and the axially mobile vacuum plunger closes tightly against the internal walls of the hollow cylinder 312. The upper side of the hollow cylinder 312 is closed through a cover plate 316. A pressure-tight feed-through for a rod 314 is provided in the cover plate 316, whereby the rod 314 is connected to the vacuum plunger 347 such that the vacuum plunger 347 can be moved in the hollow space 346 by pushing in the rod 314. Another feed-through is provided as connector 352 for a vacuum conduit 317. The vacuum conduit 317 connects the intervening space 349 and/or the hollow space 349 between the vacuum plunger 347 and the cover plate 316 to the internal space 324 of the cartridge 301. For this purpose, the vacuum conduit 317 is connected to a feed-through in the dispensing plunger 302. A pore disc 328 is provided in the feed-through and/or in the dispensing plunger 302.

Unlike the previous exemplary embodiments, the vacuum plunger 347 and the pumping plunger 344 are not directly connected to each other in the present device. Instead, a shared component 315 is provided by means of which the rod 314, and thus the vacuum plunger 347, and the pumping plunger 344 can be pushed downward (downward in FIG. 9).

A connecting conduit 238 connected via a junction 354 is connected, on the bottom, to a connector 320 for a monomer container 360. The present monomer container 360 is a metal-coated film pouch 360 that can be slit open on the inside of the connector 320 using mandrels 364 or blades. For this purpose, a lid 322 (for example a screw lid) of the monomer container 360 can be pushed onto the mandrels 364. The floor 358 of the connector 320 is inclined to allow the monomer liquid to readily flow out of the connector 320. Ventilation feed-throughs (not shown) can be provided in the lid 322 to allow air to flow in when the monomer liquid flows out into the connector 320. A screen 356 is provided in the connector 320 to be able to retain scraps or particles of the slit or punctured monomer container 360.

The monomer liquid flows from the monomer container 360 through the connecting conduit 338 into the hollow space 341. The liquid level of the monomer liquid cannot rise above the loop 314, since the same is arranged at a higher place than the junction 354. The operating element 315 is used to exert a pressure onto the pumping plunger 344. The pumping plunger 344 is used to push the monomer liquid out of the hollow space 341 into the internal space 324 of the cartridge 301. Concurrently, the operating element 315 pushes the vacuum plunger 347 downwards by means of the rod 314. In this process, the hollow space 349 is being enlarged and air is thus drawn from the internal space 324 of the cartridge 301 via the vacuum conduit 317 into the hollow space 349. The monomer liquid can be mixed with the cement powder in the internal space 324 of the cartridge 301 using the mixing facility 326. Subsequently, the cartridge 301 is separated from the connecting conduit 338 and the vacuum conduit 317. The passage through the dispensing plunger 302 can be closed for this purpose. The dispensing plunger 302 can be used to expel the ready-made mixture through the opening in the floor of the cartridge 301 from which the filter 332 has been removed. In this context, a dispensing tube (not shown) can be attached to the opening in the floor of the cartridge 301 (on the bottom in FIG. 9)

The features of the invention disclosed in the preceding description and in the claims, figures, and exemplary embodiments, can be essential for the implementation of the various embodiments of the invention both alone and in any combination.

LIST OF REFERENCE NUMBERS 1, 101, 201, 301 Cartridge
2, 102, 202, 302 Dispensing plunger
4, 104, 204, 304 Mixing rod
6, 106, 206 Handle part
8, 108, 208 Socket 10, 110, 210 Base
12, 112, 212, 312 Hollow cylinder for the vacuum plunger
14, 114, 214, 314 Rod
15 Push-button
16, 116, 216, 316 Cover plate
17, 117, 217, 317 Vacuum conduit
18, 118, 218 Connector socket
20, 120, 220, 320 Connector for the monomer container
21, 121, 221 Elastic receptacle for the monomer container/opening means
22, 122, 222, 322 Lid
24, 124, 224, 324 Internal space of the cartridge
26, 126, 226, 326 Mixing vane/mixing facility
28, 128, 228 Sterilisation plunger
29, 129, 229 Seal
30, 130, 230 Sealing plunger
32, 132, 232, 332 Powder-impermeable and liquid-permeable filter
34, 134, 234 Base connector with external thread
36, 136, 236 Cartridge connector with internal thread
38, 138, 238, 338 Connecting conduit
40, 140, 240, 340 Loop of the connecting conduit
41, 141, 241, 341 Hollow space for the pumping plunger
42, 142, 242, 342 Hollow cylinder for the pumping plunger
43, 143, 243, 343 Bottom of the hollow cylinder for the pumping plunger
44, 144, 244, 344 Pumping plunger
45, 145, 245, 345 Lower surface of the pumping plunger
46, 146, 246, 346 Open (lower) hollow space for the vacuum plunger
47, 147, 247, 347 Vacuum plunger
48, 148, 248 Seal
49, 149, 249, 349 Closed (upper) hollow space for the vacuum plunger
50, 150, 250 Opening
52, 152, 252, 352 Connector for the vacuum conduit
53, 153, 253 Seal
54, 154, 254, 354 Junction into the hollow cylinder for the pumping plunger
56, 156, 256, 356 Screen/filter
58, 158, 258, 358 Inclined floor surface of the connector for the monomer container
60, 160, 260 Glass ampoule/monomer container
62, 162, 262 Head of the glass ampoule/head of the monomer container
115 Securing facility
151 Tensioned compression spring
215 Hood
223 Ventilation passage
239 Housing for loop of the connecting conduit
315 Shared operating element
328 Closable pore filter
360 Monomer pouch/monomer container
364 Mandrel

The invention claimed is:

1. A device for the mixing of polymethylmethacrylate bone cement and/or for storage of the starting components of the bone cement, the device comprising:
   a cartridge with an internal space for mixing bone cement that is closed on one side by means of a mobile dispensing plunger;
   a monomer container for a monomer liquid and/or a connector for attachment of a monomer container for a monomer liquid such that the monomer container is openable appropriately in the device such that the monomer liquid flows from the monomer container into the device; and
   a connecting conduit through which the monomer liquid can be guided into the internal space of the cartridge, wherein a first hollow cylinder is connected to the connecting conduit and a second hollow cylinder is connected, via a vacuum conduit, to the internal space of the cartridge, wherein a pumping plunger that can be shifted axially in the first hollow cylinder is arranged in the first hollow cylinder and a vacuum plunger that can be shifted axially in the second hollow cylinder is arranged in the second hollow cylinder, wherein the pumping plunger and the vacuum plunger can be moved simultaneously, and
   further wherein the pumping plunger and the vacuum plunger are rigidly connected to each other such that, when the pumping plunger is being slid into the first hollow cylinder, the rigidly connected vacuum plunger in the second hollow cylinder moves away from the connection to the vacuum conduit.

2. The device according to claim 1, wherein the pumping plunger and the vacuum plunger are moved by means of a shared operating element.

3. The device according to claim 1, wherein the first hollow cylinder is connected to the monomer container and/or the connector for attachment of a monomer container in appropriate manner such that the monomer liquid flows from the opened monomer container or an opened attached monomer container into the first hollow cylinder and such that the connecting conduit connects the first hollow cylinder to the internal space of the cartridge in appropriate manner such that the pumping plunger can be used to push monomer liquid from the first hollow cylinder through the connecting conduit into the internal space of the cartridge by actuating the pumping plunger.

4. The device according to claim 1, wherein the first hollow cylinder is arranged between the monomer container and internal wall of the cartridge or the first hollow cylinder is arranged between the connector for the monomer container and the internal wall of the cartridge.

5. The device according to claim 1, wherein the pumping plunger and the first hollow cylinder comprise a smaller cross-sectional area than the vacuum plunger and the second hollow cylinder.

6. The device according to claim 1, wherein the pumping plunger and the vacuum plunger are connected to each other, or are affixed to each other.

7. The device according to claim 6, wherein the side of the vacuum plunger facing the vacuum conduit is arranged on the rear side of the pumping plunger and, correspondingly, the side of the pumping plunger facing the connecting conduit is arranged on the rear side of the vacuum plunger.

8. The device according to claim 1, wherein the vacuum conduit is connected to the internal space of the cartridge by means of the dispensing plunger.

9. The device according to claim 1, wherein the monomer container is arranged or arrangeable in a flexible ampoule container.

10. The device according to claim 1, wherein a mixing facility that can be operated from outside is arranged in the cartridge, wherein the mixing facility can be operated by means of a mixing rod that is guided through a feed-through in the dispensing plunger into the interior of the cartridge and is supported such as to be mobile.

11. The device according to claim 1, wherein the internal space of the cartridge contains the cement powder.

12. The device according to claim 1, wherein a filter that is impermeable for the cement powder and permeable for the monomer liquid is arranged between the connecting conduit and the internal space of the cartridge.

13. The device according to claim 1, wherein the device comprises a base, in which at least a part of the connecting conduit is arranged, wherein the cartridge is connected to the base in detachable manner, wherein a filter that is impermeable for the cement powder and permeable for the monomer liquid is arranged in the connection to the cartridge of the base.

14. The device according to claim 13, wherein the first hollow cylinder, the second hollow cylinder, and the monomer container or the first hollow cylinder, the second hollow cylinder, and the connector for attaching the monomer container are connected to the base.

15. The device according to claim 1, wherein the monomer container for the monomer liquid or the connector for attaching the monomer container merge into the first hollow cylinder on a jacket surface of the first hollow cylinder.

16. The device according to claim 1, wherein the monomer container is arranged above the connection to the first hollow cylinder.

17. The device according to claim 1, wherein the pumping plunger can be moved axially in the first hollow cylinder by hand and/or the vacuum plunger can be moved axially in the second hollow cylinder by hand.

18. The device according to claim 1, wherein the first hollow cylinder and/or the second hollow cylinder comprise an internal thread and the pumping plunger and/or the vacuum plunger comprise a matching external thread such that the pumping plunger and/or the vacuum plunger can be screwed into the first hollow cylinder and/or the second hollow cylinder in order to press the monomer liquid out of the first hollow cylinder into the internal space of the cartridge and/or to draw air out of the internal space of the cartridge into the second hollow cylinder.

19. The device according to claim 1, wherein the device comprises at least one tensioned compression spring and at least one locking mechanism, wherein the compression spring, the vacuum plunger and/or the pumping plunger is or are locked by means of the at least one locking mechanism in detachable manner, wherein the at least one compression spring, with the locking mechanism detached, exerts a pressure on the pumping plunger and/or the vacuum plunger such that the pumping plunger is pressed into the first hollow cylinder and/or the vacuum plunger is pushed away from the connector to the vacuum conduit in the second hollow cylinder.

20. The device according to claim 1, wherein the connecting conduit between the first hollow cylinder and the internal space of the cartridge comprises a loop that faces upwards, wherein the topmost point of the loop is situated above a junction of the monomer container or of the connector for the monomer container into the first hollow cylinder.

21. The device according to claim 1, wherein the volume between the vacuum plunger and the connection to the vacuum conduit in the second hollow cylinder enlarges such that the negative pressure arising in the second hollow cylinder causes a gas to flow from the internal space of the cartridge through the vacuum conduit into the second hollow cylinder.

22. The device according to claim 1, wherein the first hollow cylinder is arranged in the connecting conduit between the monomer container and the internal wall of the cartridge or the first hollow cylinder is arranged in the connector for the monomer container and the internal wall of the cartridge.

23. The device according to claim 1, wherein the vacuum plunger and the second hollow cylinder comprise a cross-sectional area at least twice as large as the pumping plunger and the first hollow cylinder.

24. The device according to claim 1, wherein the pumping plunger and the vacuum plunger are designed as a single part.

25. The device according to claim 8, wherein the dispensing plunger has a filter or a screen arranged in it by means of which the vacuum conduit is connected to the internal space of the cartridge.

26. The device according to claim 9, at least one ventilation opening is provided in the ampoule container.

27. The device according to claim 13, wherein the cartridge is connected to the base in a detachable manner by means of a screw thread.

28. The device according to claim 14, wherein the first hollow cylinder, the second hollow cylinder, and the monomer container or the first hollow cylinder, the second hollow cylinder, and the connector for attaching the monomer container are connected to the base in a non-detachable manner.

29. The device according to claim 15, wherein the monomer container for the monomer liquid or the connector for attaching the monomer container merge into the first hollow cylinder right below the pumping plunger.

30. A method for the mixing of a bone cement with the device according to claim 1, the method comprising the chronological steps of
  A) opening the monomer container of the device;
  B) flowing a monomer liquid from the monomer container into the first hollow cylinder of the device, wherein the first hollow cylinder is bounded on one side by the pumping plunger of the device;
  C) pushing the pumping plunger into the first hollow cylinder and the monomer liquid thus being pressed out of the first hollow cylinder and through the connecting conduit of the device into the internal space of the cartridge of the device, wherein a cement powder is situated in the internal space of the cartridge;
  D) moving the vacuum plunger of the device via motion of the pumping plunger, that is connected to the pumping plunger or driven parallel to same, in the second hollow cylinder of the device away from the connector of the vacuum conduit of the device, wherein gas pressure between the connector of the vacuum conduit and the vacuum plunger in the second hollow cylinder is reduced due to the motion of the vacuum plunger and gas is evacuated, through the vacuum conduit, from the internal space of the cartridge that is connected to the vacuum conduit; and
  E) mixing the monomer liquid and the cement powder in the internal space of the cartridge.

31. The method according to claim 30, wherein the air is aspirated from the internal space of the cartridge is aspirated through the vacuum conduit on the side opposite from the junction of the connecting conduit.

32. The method according to claim 30, wherein the monomer liquid and the cement powder are mixed in the internal space by means of a mixing facility by operating the mixing facility by moving a mixing rod that extends into the internal space of the cartridge and can be rotated and can be shifted in longitudinal direction.

33. The method according to claim 30, wherein the pumping plunger is pushed into the first hollow cylinder by means of a tensioned elastic spring element and/or the vacuum plunger is moved in the second hollow cylinder by means of a tensioned elastic spring element.

34. The method according to claim 30, wherein the cartridge containing the ready-mixed cement dough is detached from the connecting conduit, vacuum conduit, first hollow cylinder, second hollow cylinder and monomer container, and the ready-mixed cement dough is dispensed from the internal space of the cartridge through propulsion of a dispensing plunger, which is supported in the cartridge such as to be axially mobile and forms a boundary of the internal space of the cartridge on one side.

\* \* \* \* \*